United States Patent [19]

Parsons et al.

[11] Patent Number: 5,099,063
[45] Date of Patent: Mar. 24, 1992

[54] CERTAIN PHOSPHINIC ACID DERIVATIVES HAVING ANTIBACTERIAL ACTIVITY

[75] Inventors: William H. Parsons, Rahway; Arthur A. Patchett, Westfield; William R. Schoen, Edison, all of N.J.; Masao Taniguchi, Machida, Japan

[73] Assignee: Merck & Co., Inc., Rahway, N.J.

[21] Appl. No.: 541,167

[22] Filed: Jun. 21, 1990

Related U.S. Application Data

[63] Continuation of Ser. No. 284,754, Dec. 12, 1988, abandoned, which is a continuation of Ser. No. 927,208, Nov. 5, 1986, abandoned.

[51] Int. Cl.$^5$ .............................. C07F 9/30; C07F 9/32
[52] U.S. Cl. ........................ 562/16; 558/169; 560/153; 560/155; 546/22
[58] Field of Search ............... 562/16; 560/155, 153; 558/169

[56] References Cited

U.S. PATENT DOCUMENTS

| | | | |
|---|---|---|---|
| 4,147,780 | 4/1979 | Dingwall | 514/114 |
| 4,160,452 | 7/1979 | Theeuwes | 424/427 |
| 4,256,108 | 3/1981 | Theeuwes | 424/424 |
| 4,265,874 | 5/1981 | Bonsen et al | 424/473 |
| 4,374,131 | 2/1983 | Petrillo | 514/89 |
| 4,416,833 | 11/1983 | Karanewsky et al. | 558/179 |
| 4,539,208 | 9/1985 | Kahen et al. | 514/195 |
| 4,715,994 | 12/1987 | Parsons et al. | 562/16 |

OTHER PUBLICATIONS

F. Arndt Organic Syn. Coll. V II 165-167 p. 33 (1943).
F. R. Atherton et al., Antimibrobial Agents & Chemoth. 15. 677 (1979).
P. A. Bartlett and W. B. Kezer J. Amer. Chem. Soc. 106 4282-4283 (1979).
E. K. Baylis et al., J. Chem. Soc. Perkin Trans 1 2845-2853 (1984).
M. Bergmann & H. Schleich. Z. Physiol. Chem. Soc 205 pp. 65-75 (1966).
B. J. Campbell et al Biochem Biophys Acta 118 pp. 371-386 (1966).
Chem Abstracts, vol. 107, No. 11, No. 97134K (1987).
Chem Abstracts, vol. 107 (9) No. 78205d (1987).
Chaiet et al., J. Antibiotics 37 (3) 207-210 (1984).
Gundermann et al., Chem. Bes. 94 3254 (1961).
F. M. Kahan et al., J. Antimicrobial Chemo. 12, Suppl. D, 1-35 (1983).
Lesiak et al., Polish J. Chem. 53 327 (1979).
Neuhaus J. Biol. Chem., 778 (1962).
F. C. Neuhaus & W. P. Hammes, Pharm. Ther. 14 265-319 (1981).
F. C. Neuhaus & J. L. Lynch Biochemistry 3 471-480 (1964).
F. C. Neuhaus et al., Biochemistry 8 5119-5124 (1969).
A. Rahman et al., Tetrahedron 36 1063-1070 (1980).
E. D. Thorsett et al., (Merck & Co., Inc. Proc. Natl. Acad. Sci. U.S.A. vol. 79 2176-2180 (Apr. 1982).
J. K. Thottathil et al., Tetrahedron Lett. 25 4737-40, 4741-44 (1984).

*Primary Examiner*—Alan L. Rotman
*Attorney, Agent, or Firm*—Frank P. Grassler; John W. Harbour; Hesna J. Pfeiffer

[57] ABSTRACT

New 3-(1-aminoalkylphosphinyl)-(2-substituted)propionic acids are described which display antibacterial activity and potentiate carbapenem antibiotics.

13 Claims, No Drawings

CERTAIN PHOSPHINIC ACID DERIVATIVES HAVING ANTIBACTERIAL ACTIVITY

This is a continuation of application Ser. No. 07/284,754, filed Dec. 12, 1988, abandoned, which is a continuation of Ser. No. 06/927,208, filed Nov. 5, 1986, abandoned.

BACKGROUND OF THE INVENTION

1. Field of the Invention

This invention relates to new antibacterial agents which interfere in bacterial cell wall synthesis by inhibiting the enzyme D-Ala-D-Ala ligase. Compounds of this invention also inhibit renal dehydropeptidase (DHP) and, therefore, potentiate the antibiotic activity of carbapenem antibiotics.

2. Brief Description of the Art

Many antibacterial agents owe their selective toxicity to the fact that their targets are structures which are only present in the sensitive bacterium. One of these structures is peptidoglycan a cell wall polymer which plays a vital role in protecting bacteria from lysis. A number of agents, e.g., β-lactams, bacitracin, and flavomycin, interfere with the assembly of this polymer by inhibiting enzymatic reactions involved in the final stages of assembly.

Peptidoglycan biosynthesis involves a Precursor, UDP-MurNAc-Ala-D-Glu-Lys-D-Ala-D-Alanine that is biosynthesized in a multienzyme pathway which terminates in the addition of D-Alanine-D-Alanine to the UDP-MurNAc-tripeptide. The formation of D-Alanyl-D-Alanine is catalyzed by D-Alanyl-D-Alanine ligase (synthetase). It is known that inhibition of D-Alanyl-D-Alanyl ligase will terminate peptidoglycan biosynthesis resulting in vivo in bacterial cell lysis. Such inhibitors can serve as antibacterials. For example, D-Cycloserine, a D-Alanine mimic, is a reversible inhibitor of the ligase at both the donor and acceptor sites and is the most potent ligase inhibitor described heretofore, and is a potent antibacterial. (F. C. Neuhaus et al., *Biochemistry* 3, 471–480 (1964)).

Dipeptide analogs of D-Alanyl-D-Alanine are also known to be inhibitors of ligase. (F. C. Neuhaus et al., *Biochemistry* 8, 5119–5124 (1965), and F. C. Neuhaus and W. P. Hammes, *Pharmac. Ther.* 14. 264–319 (1981)).

Renal dehydropeptidase (E.C. 3.4.13.11) is a mammalian enzyme which metabolizes carbapenem antibiotics such as thienamycin and imipenem. Inhibition of this enzyme enhances the urinary recovery of these antibiotics and reduces their renal toxicity. EPO Publication No. 0091594 to Sanraku-Ocean Co., Ltd. describes aminocarboxylic acid derivatives possessing dipeptidase inhibiting activity. This subject and the development of cilastatin as a renal dehydropeptidase inhibitor for use in combination with imipenem have also been reviewed by F. M. Kahan et al., *J. Antimicrobial Chemotherapy*, 12, Suppl. D, 1–35 (1983).

U.S. Pat. No. 4,374,131 to Petrillo (assigned to E. R. Squibb & Sons, Inc.) discloses amino and substituted amino phosphinyl-alkanoyl compounds which are useful hypertensive agents due to their angiotensin-converting-enzyme (ACE) inhibition activity.

E. D. Thorsett et al., (Merck & Co., Inc.) *Proc. Natl. Acad. Sci. USA* Vol. 79, pp 2176–2180 (April 1982) discloses phosphorus containing inhibitors of angiotensin-converting enzyme.

With this background, the search for newer and more effective antibacterial agents which are ligase inhibitors, is a continuing one.

SUMMARY OF THE INVENTION:

It has been found that compounds of Structures I and II, shown below, are inhibitors of D-Alanyl-D-Alanine ligase, and are useful in the treatment of bacterial infections. These compounds may be administered alone or in combination with other antibiotics such as D-cycloserine or β-lactam antibiotics. These compounds also inhibit renal dehydropeptidase E.C. (3, 4, 13, 11) and are useful to potentiate the in vivo effects of penem and carbapenem antibiotics such as imipenem.

By this invention there is provided phosphinodipeptides of formulas I and II;

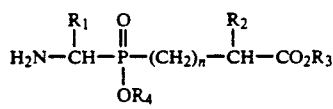

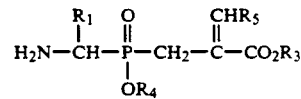

wherein:

$R_1$ is H or $CH_3$;

$R_2$ and $R_5$ are selected from (a) hydrogen, (b) $C_1C_{12}$ linear or branched alkyl;

(c) $C_2$-$C_{12}$ linear or branched monoalkenyl;

(d) $C_7$-$C_{20}$ aralkyl, wherein the alkyl chain is linear or branched $C_1$-$C_8$;

(e) heterocyclic alkyl, wherein the alkyl chain is linear or branched $C_1$-$C_8$ and the heterocyclic ring is 5–6 membered, optionally fused with a benzene ring, fully aromatic, and containing 1–3 O, N or S heteroatoms;

wherein said above groups for $R_2$ and $R_5$ can be substituted by one or more: halo, hydroxy, carboxy, $C_1$-$C_4$ alkoxycarbonyl, $C_7$-$C_{16}$ arylalkoxycarbonyl, $C_3$-$C_7$ cycloalkyl, $C_1$-$C_4$ alkoxy, $C_6$-$C_{12}$ aryloxy, amino, mono- or di-$C_1$-$C_8$ alkylamino, thio, $C_1$-$C_4$ alkylthio, $C_6$-$C_{12}$ arylthio, $C_7$-$C_{16}$ aralkylthio, or the radical —S—$(CH_2)_n$-CH(NH$_2$)COOH, where $n = 1-2$;

with the proviso that $R_2$ or $R_5$ is at least $C_2$ alkyl if substituted by one of the above-defined thio groups, and wherein the aryl or aromatic heterocyclic rings can be further substituted by $C_1$-$C_4$ linear or branched alkyl, trihalomethyl, nitro, halo, cyano or sulfonamido;

$R_3$ and $R_4$ are hydrogen, $C_1$-$C_4$ alkyl, $C_6$-$C_{12}$ aryl or $C_7$-$C_{16}$ aralkyl; and including stereoisomers and racemates thereof.

Also provided is a pharmaceutical composition useful in the treatment of antibacterial infections which comprises a pharmaceutically acceptable carrier and a pharmaceutically effective amount of an antibacterial compound of formulae I or II, or mixture thereof:

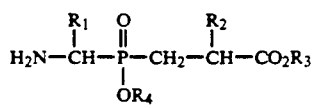

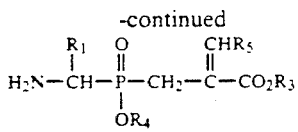

wherein:

R₁ is H or CH₃;

R₂ and R₅ are as defined above;

R₃ and R₄ are independently selected from hydrogen, lower alkyl, aryl lower alkyl;

wherein the carbon atom (linked to phosphorus) attached to R₁ is in the D(S) or DL(SR) stereoconfiguration; to R₂, in the D(R) or DL(RS) stereoconfiguration; and if R₅ is present the double bond is in the E or Z configuration.

Preferred embodiments of Structures I and II for antibacterial activity include: R₁ is methyl; R₂ and R₅ are small radicals such as methyl, ethyl, bromomethyl, chloromethyl and the like; and the carbon attached to R₁ is in the D(S) stereoconfiguration.

Further provided is a pharmaceutical composition useful in the treatment of antibacterial infections which comprises a pharmaceutically effective amount of a DHP-inhibiting compound of Formula I or II, or mixture thereof, in combination with a pharmaceutically effective amount of a carbapenem or penem antibiotic:

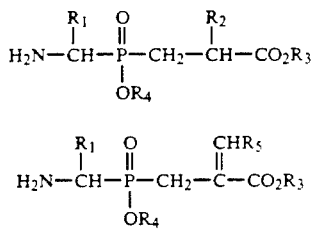

wherein:

R₁ is H or CH₃;

R₂ and R₅ are as defined above;

R₃ and R₄ are independently selected from hydrogen, lower alkyl, aryl lower alkyl; and the carbon (linked to phosphorus) attached to R₁ is in the L(R) or DL(RS) configuration; the carbon attached to R₂ is in the D(R), L(S) or DL(RS) configuration; and if R₅ is present, the double bond is in the E or Z configuration.

Preferred embodiments of Structure I and II for DHP inhibiting activity are where, R₁ is methyl; R₂ and R₅ are long chain alkyl groups, such as n-heptyl, n-hexyl, which can be substituted with groups such as halo, hydroxy, carboxy, C₁-C₄ alkoxycarbonyl, C₇-C₁₆ arylalkoxycarbonyl, C₃-C₇ cycloalkyl, C₁-C₄ alkoxy, C₆-C₁₂ aryloxy, amino, mono- or di-C₁-C₈ alkylamino, thio, C₁-C₄ alkylthio, C₆-C₁₂ arylthio, C₇-C₁₆ aralkylthio, or the radical —S—(CH₂)ₙ—CH(NH₂)COOH, where n=1-2; with the proviso that R₂ or R₅ is at least C₂ alkyl if substituted by one of the above-defined thio groups, and wherein the aryl or aromatic heterocyclic rings can be further substituted by C₁-C₄ linear or branched alkyl, trihalomethyl, nitro, halo, cyano or sulfonamido; the chain carbon (alpha to phosphorus) attached to R₁ is Preferably of L (R) stereoconfiguration; and if R₅ is present, it is in the Z stereoconfiguration.

DESCRIPTION OF THE INVENTION AND PREFERRED EMBODIMENTS

The novel compounds of the above Structural Formulas I and II represent new and useful antibacterial agents and dehydropeptidase inhibitors.

The values of the alkyl and alkenyl groups for R₂ and R₅, except where noted otherwise, represented by any of the variables include linear or branched, alkyl and monoalkenyl and chain hydrocarbon radicals from one to twelve carbon atoms, for example, methyl, ethyl, n-propyl, isopropyl, n-butyl, isobutyl, sec-butyl, t-butyl, n-pentyl, isopentyl, n-heptyl, n-nonyl, 4,4-dimethylpentyl, or vinyl, allyl, 1-butenyl, 2-butenyl, 5-hexenyl and the like. Preferred for antibacterial activity are ethyl and chloromethyl. Preferred for DHP inhibition are n-butyl, n-pentyl, n-heptyl or 1-butenyl.

The aralkyl group represented by the above variables has from one to eight carbon atoms in the alkyl portion and "aryl" where noted, represents phenyl, naphthyl, or biphenyl. Representative examples include benzyl, phenethyl, 4-phenyl-n-butyl, δ-phenyl-n-octyl, and the like.

The aromatic heterocyclic, i.e. "heteroaryl" substituent, are synonymous, and recited above represents a 5- or 6-membered aromatic ring containing from one to three O, N or S heteroatoms, preferably one O or S and/or 1-3 N heteroatoms, such as, for example, pyridyl, thienyl, furyl, imidazolyl, and thiazolyl as well as any bicyclic group derivable therefrom in which any of the above heterocyclic rings is fused to a benzene ring such as, for example, indolyl, quinolinyl, isoquinolinyl, benzimidazolyl, benzothiazolyl, benzofuryl, and benzothienyl.

The named substituents on the alkyl and alkenyl chains can be present on the aromatic rings in the aralkyl, heterocyclic alkyl and heteroaryl groupings as well. Site of substitution includes all available sites and substitution can involve one or more of the same or different groups.

The substituents are: halo, meaning fluoro, chloro, bromo or iodo; hydroxy; carboxy; C₁-C₄ linear or branched alkoxycarboxy, e.g. methoxycarbonyl and ethoxycarbonyl; C₇-C₁₆ arylalkoxy carbonyl, e.g. benzyloxycarbonyl, n-butyloxycarbonyl; C₃-C₇ cycloalkyl, e.g. cyclopentyl and cyclohexyl; C₁-C₄ alkoxy, e.g. t-butoxy and ethoxy; C₆-C₁₂ aryloxy, e.g. biphenyloxy, benzyloxy; amino; mono- or di-C₁-C₈ dialkylamino, e.g. methylamino, isopropylamino, n-butylamino, isohexylamino, N,N-diethylamino, methylethylamino, methyl-t-butylamino, di-n-octylamino; thio; C₁-C₄ alkylthio, e.g. methylthio, ethylthio; C₆-C₁₂ arylthio, e.g. phenylthio; C₇-C₁₆ aralkylthio, e.g. benzylthio, naphthylmethylthio; the radicals —S—CH₂—CH(NH₂)COOH and —S—(CH₂)₂—CH(NH₂)COOH, both preferably in the L-configuration; and, where a thio substituent is present, R₂/R₅ must be at least a C₂ alkyl grouping. Where an aryl or heteroaryl group is present in the substituent, the ring carbons can additionally be substituted by one or more of linear or branched C₁-C₄ alkyl, e.g. methyl, ethyl, isopropyl, t-butyl; trihalomethyl, "halo" having the same meaning as described above, e.g. trichloromethyl, trifluoromethyl; nitro, cyano or sulfonamide.

Preferred are the compounds wherein:

R₁ is methyl;

R₂ and R₅ are:

C₁-C₁₀ linear or branched alkyl; C₇-C₁₄ aralkyl;

wherein both groups can be substituted with halo, amino, mono- or di-$C_1$-$C_4$ linear or branched alkylamino, carboxyl, $C_1$-$C_4$ alkoxycarbonyl, hydroxy, $C_1$-$C_4$ alkoxy, $C_5$-$C_6$ cycloalkyl, $C_6$-$C_{10}$ aryloxy, thio, $C_1$-$C_4$ linear or branched alkylthio, $C_6$-$C_{10}$ arylthio, $C_7$-$C_{14}$ aralkylthio, $-S-(CH_2)_n-CH(NH_2)CO_2H$, where n=1-2, with the proviso that $R_2$ or $R_5$ is at least $C_2$ alkyl if substituted by one of the above-defined thio groups and wherein the aryl group ring carbons can further be substituted by linear or branched $C_1$-$C_4$ alkyl; $R_3$ and $R_4$ are hydrogen, $C_1$-$C_4$ linear or branched alkyl e.g. methyl, ethyl, or $C_7$-$C_{14}$ aralkyl e.g. benzyl.

Preferred compounds of Structure I for antibacterial activity include those in which the stereochemical configurations of the carbon (linked to phosphorus) attached to $R_1$ are D(S), DL(SR), and the chain carbon attached to $R_2$ are, respectively, D(R), DL(RS). Particularly preferred is where the stereochemical configurations of the carbons attached to $R_1$ and $R_2$ are D(S) and D(R) respectively.

Preferred compounds of Structure II for antibacterial activity include those in which the stereochemical configuration of the carbon atom attached to $R_1$ is D and the configuration of the double bond is Z or E.

The preferred compounds of Structures I or II, for use as DHP inhibiting agents include those having the carbon attached to $R_1$ in the L(R) configuration and the carbon attached to $R_2$ in the D(R) or L(S) configuration and if $R_5$ is present, the double bond is preferred in the Z configuration.

The Formulas I and II compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine and N-methyl-D-glucamine, and salts with amino acids such as arginine, lysine, and so forth. Water or oil-soluble or dispersible products are thereby obtained.

Further embodiments of this invention are the use of the compounds of formulas I and II as antibacterials agents administered separately or in combination with other antibacterials such as D-cycloserine, fosfomycin, pentizidone, cefoxitin, ceftazidine, thienamycin, imipenem, ampicillin, and the like.

The pharmaceutical composition useful in the treatment of antibacterial infections preferably comprises a pharmaceutically acceptable carrier and a pharmaceutically effective amount of an antibacterial compound of formulae I or II, or mixture thereof: wherein the compound contains the carbon atoms attached to $R_1$ and $R_2$ in the D configuration and if $R_5$ is present, the double bond is in the E or Z configuration.

Specific preferred antibacterial compounds useful in the composition include: 1-(aminoethyl)-(2-carboxy-n-propyl) phosphinic acid, 1-(aminoethyl)-(2-carbomethoxy-n-propyl) phosphinic acid, 1-(amino-ethyl)-(2-carboxy-n-butyl) phosphinic acid, 1-(amino-ethyl)-(2-carboxy-5-phenyl-n-pentyl) phosphinic acid, 1-(aminoethyl)-(2-carboxy-n-nonyl) phosphinic acid, 1-(aminoethyl)-(2-carboxy-5-(4-pyridyl)-n-pentyl) phosphinic acid, 1-(aminoethyl)-(2-carboxy-3-chloro-n-propyl) phosphinic acid, 1-(aminoethyl)-(2-carboxy-3-bromo-n-propyl) phosphinic acid, 1-(aminoethyl)-(2-carboxy-n-hexyl) phosphinic acid, 1-aminoethyl-(2-carboxy-2-n-octenyl) phosphinic acid, 1-(amino-ethyl)-(2-carboxy-2-propenyl) Phosphinic acid, 1-(aminoethyl)-(2-carboxy-4-phenyl-2-butenyl) phosphinic acid, and 1-(aminoethyl)-(2-carboxy-5-Phenyl-2-pentenyl) phosphinic acid.

The pharmaceutical composition can further comprise an effective amount of a second antibacterial compound in combination selected from. D-cycloserine, fosfomycin, pentizidone, cefoxitin, ceftazidine, thienamycin, imipenem, ampicillin, and the like.

Also provided is a method for treating a bacterial infection in a mammalian host comprising administering to said host a therapeutically effective amount of the above-described composition.

In pharmaceutical compositions useful in the treatment of antibacterial infections which comprise a pharmaceutically effective amount of a compound of Formula I or II, or mixture thereof, in combination with a pharmaceutically effective amount of a carbapenem or penem antibiotic the carbon attached to $R_1$ in the L(R) configuration and the carbon attached to $R_2$ in the D(R) or L(S) configuration and if $R_5$ is present, the double bond is preferred in the Z configuration.

Specifically preferred DHP-inhibiting compounds useful in the composition include: -(aminoethyl)-(2-carboxy-n-propyl) phosphinic acid, -(aminoethyl)-(2-carbomethoxy-n-propyl) phosphinic acid, 1-(aminoethyl)-(2-carboxy-n-butyl) phosphinic acid, 1-(aminoethyl)-(2-carboxy-5-phenyl-n-pentyl-n-propyl) phosphinic acid, 1-(aminoethyl)-(2-carboxy-n-nonyl) phosphinic acid, 1-(aminoethyl)-(2-carboxy-5-(4-pyridyl)-n-Pentyl) phosphinic acid, 1-(aminoethyl)-(2-carboxy-3-chloro-n-propyl) phosphinic acid, -(aminoethyl)-(2-carboxy-3-bromo-n-propyl) phosphinic acid, 1-(aminoethyl)-(2-carboxy-n-hexyl) phosphinic acid, 1-(aminoethyl)-(2-carboxy-2-n-octenyl) phosphinic acid, 1-(aminoethyl)-(2-carboxy-2-propenyl)-phosphinic acid, 1-(aminoethyl)-(2-carboxy-4-phenyl-2-butenylpropyl)-phosphinic acid, and 1-(aminoethyl)-(2-carboxy-5-phenyl-2-pentenyl) phosphinic acid.

Also provided is a method for treating a bacterial infection in a mammalian host comprising administering to said host a therapeutically effective amount of the above-described composition.

D-Alanyl-D-Alanine Ligase In Vitro Activity

The ligase enzyme inhibitory activity of compounds of Formula I have been evaluated in vitro with only minor modifications of the procedures of F. C. Neuhaus (*Biochemistry* 3, 471–480 (1964) and references cited therein) using D-cycloserine as a control and standard ligase inhibitor. The procedure is as follows:

D-ALANYL-D-ALANINE LIGASE METHOD:

*Streptococcus faecalis* (ATCC 8043) was grown as described by Neuhaus (J. Biol. Chem., 237:778, 1962). Cell-free extracts were prepared by sonication followed by centrifugation at 27,000×g for 30 minutes. Protein was precipitated with 55% ammonium sulfate. The precipitate was dissolved in 0.05M Tris-Cl buffer (PH 7.0), dialyzed against 0.0025M glutathione and stored in liquid nitrogen. No loss of activity was observed after 1 year.

The assay mixture contained 0.05M Tris-Cl buffer (pH 7.9), 0.01M KCl, 0.008M $MgCl_2$, 0.005M ATP, 0.005M (14C-1)-D-alanine and 5 µof enzyme (specific activity = 0.38 units/mg protein). Assay volume was 0.1 ml.

Inhibitors were pre-incubated with enzyme, $MgCl_2$, KCl and buffer, for 40 minutes at room temperature, before addition of ATP and substrate. Samples were subsequently incubated at 37° C for 30 minutes.

Twenty µl of each sample was applied to the preabsorbent layer of high resolution, pre-channeled silica-gel TLC plates to stop the reaction. Plates were developed in ethanol:ammonium hydroxide: $H_2O$ (11:1:8) for 2-3 hours and the radioactive zones located and integrated with a Berthold Linear Analyzer. $IC_{50}$'s were determined for active compounds ( 70% inhibition) in ethanol:ammonium hydroxide: $H_2O$ (11:1:18) for 2-3 hours and the radioactive zones located and integrated with Berthold Linear Analyzer. $IC_{50}$'s were determined for active compounds ( 70% inhibition).

Representative test data with compounds of this invention using the above procedure are shown below.

| D-Ala—Ala Ligase Inhibition | | | |
|---|---|---|---|
| $$H_2N-\overset{CH_3}{\underset{\underset{OH}{|}}{CH}}-\overset{O}{\overset{\|}{P}}-CH_2-\overset{R_2}{\underset{|}{CH}}-CO_2R_3$$ | | | |
| Stereochemistry at the methyl position | $R_2$ (DL) | $R_3$ | $IC_{50}$ (µM) |
| DL | H | H | 535 |
| DL | methyl | H | 165 |
| D | methyl | H | 124 |
| DL | methyl | methyl | 60 |
| DL | ethyl | H | 50 |
| D | ethyl | H | 45 |
| DL | phenylpropyl | H | 20 |
| DL | n-heptyl | H | 12.5 |
| D | n-heptyl | H | 4 |

| D-Ala—Ala Ligase Inhibition | | |
|---|---|---|
| $$H_2N-\overset{CH_3}{\underset{\underset{OH}{|}}{CH}}-\overset{O}{\overset{\|}{P}}-CH_2-\overset{CHR_5}{\overset{\|}{C}}-CO_2H$$ | | |
| Stereochemistry at the methyl position | $R_5$ | $IC_{50}$ (µM) |
| D | H | 210 |
| DL | n-pentyl, (E,Z isomers) | 700 |
| DL | benzyl (E isomers) | 210 |

II. In Vitro Antibacterial Assay of Compounds of Formulas I & II

The antibacterial data shown below were obtained using a synthetic agar medium described by F. R. Atherton et al., *Antimicrobial Agents and chemotherapy*, 15, 677 (1979).

ANTIBACTERIAL RESULTS
(Minimum Inhibitory Concentrations from Agar Dilution Assays in mg/ml)

$$H_2N-\overset{CH_3}{\underset{\underset{OH}{|}}{CH}}-\overset{O}{\overset{\|}{P}}-CH_2-\overset{R_2}{\underset{|}{CH}}-CO_2R_3 \text{ and } H_2N-\overset{CH_3}{\underset{\underset{OH}{|}}{CH}}-\overset{O}{\overset{\|}{P}}-CH_2-\overset{CHR_5}{\overset{\|}{C}}-CO_2R_3$$

| Stereochemistry of methyl $R_2$ (DL) | DL methyl | D methyl | DL methyl | D ethyl | DL phenyl-propyl | D n-heptyl | D Cl—$CH_2$— | D — |
|---|---|---|---|---|---|---|---|---|
| $R_3$ | H | H | methyl | H | H | H | H | H |
| $R_5$ | — | — | — | — | — | — | — | H |
| Staph. aureus-2865 | >256 | >256 | >256 | >256 | >256 | 128 | >256 | >256 |
| Strep. faecalis-2864 | — | 64 | 128 | 16 | 256 | 64 | 128 | 256 |
| E. coli TEM 2+ | 128 | 256 | 256 | 64 | " | 128 | " | >256 |
| E. coli DC2 | 128 | 256 | 64 | 32 | 128 | 32 | " | " |
| E. coli | >256 | >256 | >256 | 128 | " | 128 | >256 | " |
| Sal. typh. | " | " | " | 256 | " | 128 | " | " |
| Ent. cloacae | " | " | 256 | 128 | >256 | 256 | 256 | " |
| Klebs. pneum. | " | 256 | >256 | 256 | 256 | 64 | 128 | 64 |
| Prot. vulg. | " | " | 256 | 128 | >256 | 128 | 64 | >256 |
| Pseud. aerug. | " | 128 | 128 | 32 | " | >256 | 16 | 128 |
| Serratia marcescens | " | >256 | >256 | >256 | " | " | >256 | >256 |

Compounds of this invention also inhibit dehydropeptidase-I (renal dipeptidase, EC 3.4.13.11) and, therefore, potentiate the antibiotic activity of carbapenem antibiotics. Renal dehydropeptidase activity was first described by M. Bergmann and H. Schleich, *Z. Physiol. Chem.*, 205. 65 (1932); see also B. J. Campbel et al., *Biochim. biophys. Acta.*, 118 371 (1966) and references therein.

In order to demonstrate the ability of the compounds of Formula I to suppress the action of the renal dipeptidase enzyme, an in vitro screen procedure was followed. This measured the ability of compounds to inhibit hydrolysis of glycyldehydrophenylalanine (GDP) by a solubilized preparation of dipeptidase isolated from hog kidneys. The procedure is as follows: to a 1 ml system containing 50 mM "MOPS" (3-(N-morpholino)-propanesulfonic acid) buffer, pH 7.1, is added 5 µg of lyophilized enzyme, and the test compound at a final concentration of 0.1 mM. After a five minute incubation at 37° C, GDP is added to a final concentration of 0.05 mM. Incubation is continued for 10 minutes, at 37° C and hydrolysis of GDP is measured by the change in optical density with time at 275 nm. Inhibition of the enzyme is gauged by comparison to a standard run containing no inhibitor and is expressed as the inhibitor binding constant, $K_i$. This is the concentration of the inhibitor which achieves 50% inhibition of enzyme.

The table below summarizes some representative data with compounds of this invention.

RENAL DEHYDROPEPTIDASE I INHIBITION $$H_2N-\underset{\underset{CH_3}{|}}{CH}-\underset{\underset{OH}{|}}{\overset{\overset{O}{\|}}{P}}-CH_2-\underset{\underset{R_2}{|}}{CH}-CO_2H$$

| Stereochemistry of methyl | $R_2$(DL) | $K_i$(nM) |
|---|---|---|
| DL | methyl | 10 |
| L | methyl | 10 |
| D | methyl | 140 |
| DL | n-butyl | 4 |
| L | phenylpropyl | 27 |
| D | phenylpropyl | 1000 |
| DL | 4-pyridylpropyl | 12 |

$$H_2N-\underset{\underset{CH_3}{|}}{CH}-\underset{\underset{OH}{|}}{\overset{\overset{O}{\|}}{P}}-CH_2-\overset{\overset{CHR_5}{\|}}{C}-CO_2H$$

| Stereochemistry of methyl | $R_5$ | E/Z | $K_i$(nM) |
|---|---|---|---|
| D | H | — | 230 |
| L | H | — | 27 |
| DL | n-pentyl | mixt. | 5.8 |
| DL | phenethyl | Z | 16 |
| DL | phenethyl | E | 7 |

The in vivo effectiveness of DHP to increase the metabolic stability of carbapenem antibiotics can be demonstrated by measuring the urinary recovery of such antibiotics in the presence and absence of coadministered dehydropeptidase inhibitor. For example, see F. M. Kahan et al., J. Antimicrobial Chemotherapy, 12, Suppl. D, 1-35 (1983). It is also possible to observe this potentiation by measuring the dosage required to treat infections in animals with a dehydropeptidase susceptible antibiotic alone or in combination with a dehydropeptidase inhibitor.

For administration, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the compounds of the invention.

The present compositions can be administered parenterally and this is preferred when they are used in combination with a carbapenem antibiotic such as imipenem. They may also be administered orally. The compounds of this invention may also be used to treat topical antibacterial infection. Therefore, these compounds may be presented in a number of appropriate dosage forms; e.g., tablets, capsules, suspensions, solutions, and the like, for oral administration; solutions, suspensions, emulsions, and the like, for P/1106A - 22 - 17313 parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
 (a) a naturally-occurring phosphatide such as lecithin,
 (b) a condensation product of an alkylene oxide with a fatty acid, for example, polyoxyethylene stearate,
 (c) a condensation product of ethylene oxide with a long chain aliphatic alcohol, for example, heptadecaethyleneoxycetanol,
 (d) a condensation product of ethylene oxide with a partial ester derived from a fatty acid and a hexitol such as polyoxyethylene sorbitol monooleate, or
 (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3)esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

For topical use, creams, ointments, jellies, solutions or suspensions, etc., containing the compositions of the invention are employed.

Treatment dosage for human beings can be varied as necessary. Generally, oral dosages of the antibacterial compounds of this invention when given orally are in the range 250 mg to 4 g per patient given 3-4 times daily. The intravenous or intramuscular dosages are 100 mg to 1 g given 3-4 times daily. When the compounds of the invention are given intravenously or intramuscularly to potentiate carbapenem antibiotics such as imipenem they are given in combination with the antibiotic in amounts of 0.1-10 mg/kg/day.

The amount of active ingredient that may be combined with the carrier materials to produce a single dosage form will vary depending upon the host treated and the particular mode of administration. For example, a formulation intended for oral administration may contain, for example, from 100 mg to 2000 mg of active agent compounded with an appropriate and convenient amount of carrier material which may vary from about 5 to about 95 percent of the total composition.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of Formula I can be prepared by the methods shown in the following Reaction Scheme wherein $R^1$, $R^2$ and $R^3$ are as defined above unless otherwise indicated.

As will be evident to those skilled in the art and as demonstrated in the Examples hereinafter, reactive groups not involved in the Examples hereinafter, reactive groups not involved in the reactions, such as amino, carboxy, mercapto, etc., may be protected by methods standard in peptide chemistry prior to the coupling reactions and subsequently deprotected to obtain the desired products. Cbz refers to carbobenzyloxy.

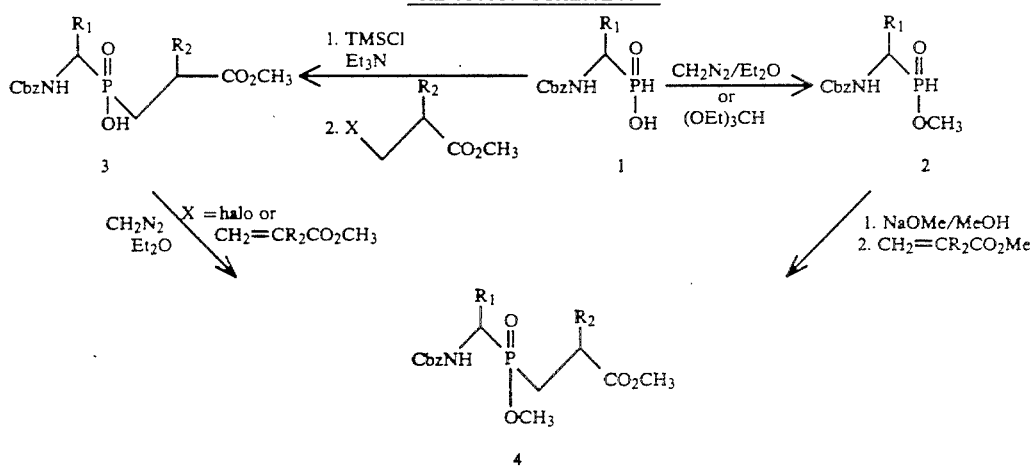

REACTION SCHEME A:

The Cbz aminoalkylphosphonous acids (1) can be prepared according to procedures described by P. A.

Bartlett et al. (*J. Amer. Chem. Soc.* 106, 4282-4283 (1984)) and E. K. Baylis et al. (*J. Chem. Soc. Perkin Trans.* 1, 2845-2853 (1984)) and can be resolved to give optically active materials by the method of Baylis (reference above) both methods hereby incorporated by reference. Compounds derived from both the optically active and racemic materials are claimed in the present invention.

acid (1) with appropriately substituted 3-halopropionates or acrylates in the presence of a trialkylsilylchloride such as trimethylsilylchloride and a tertiary amine such as triethylamine according to the general methods of J. K. Thottathil et al. (*Tetrahedron lett.* 25, 4737-40, 4741-44 (1984), hereby incorporated by reference.

The phosphinic acid 3 may be esterified by diazomethane to give compound 4.

REACTION SCHEME B:

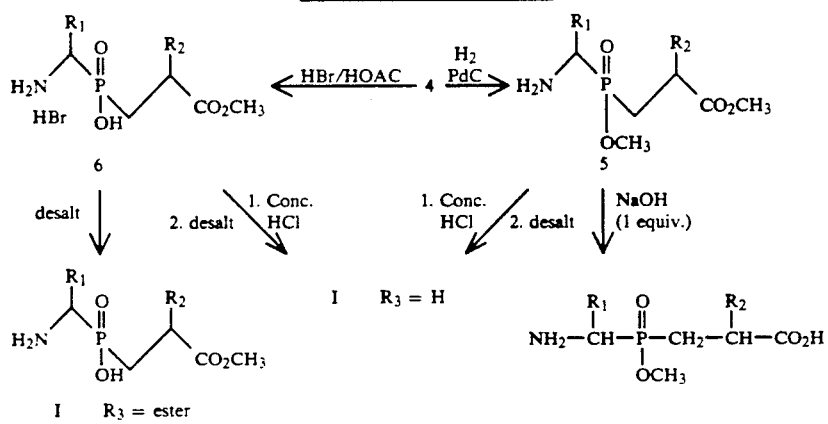

The protected aminoalkylphosphonous acid (1) is esterified with either diazomethane or triethylorthoformate to give the methyl or ethyl ester (21) which is deprotonated with either sodium methoxide or ethoxide in the corresponding alcohol and treated with the appropriately substituted acrylate to give (4), the protected form of Formula I. The acrylates can be prepared by procedures outlined by J. Harley-Mason in Tetrahedron 36, 1036-1070 (1980), hereby incorporated by reference.

Compound 4 can be alternatively synthesized by alkylation of the protected aminoalkylphosphonous Compound 4 is converted to formula I by two standard routes. The carbobenzyloxy group can be removed by either hydrogenation in an alcohol such as ethanol with a catalyst such as Pd/C, or by cleavage with HBr in acetic acid. Subsequent ester hydrolysis in concentrated HCl provides after treating with propylene oxide, for example, compounds of formula I ($R_3$=H). The carboxyester ($R_3$=alkyl) can be isolated by desalting ester hydrobromide 6. The phosphinic ester ($R_4$=alkyl) can be isolated by selective hydrolysis of carboxyester 5.

REACTION SCHEME C:

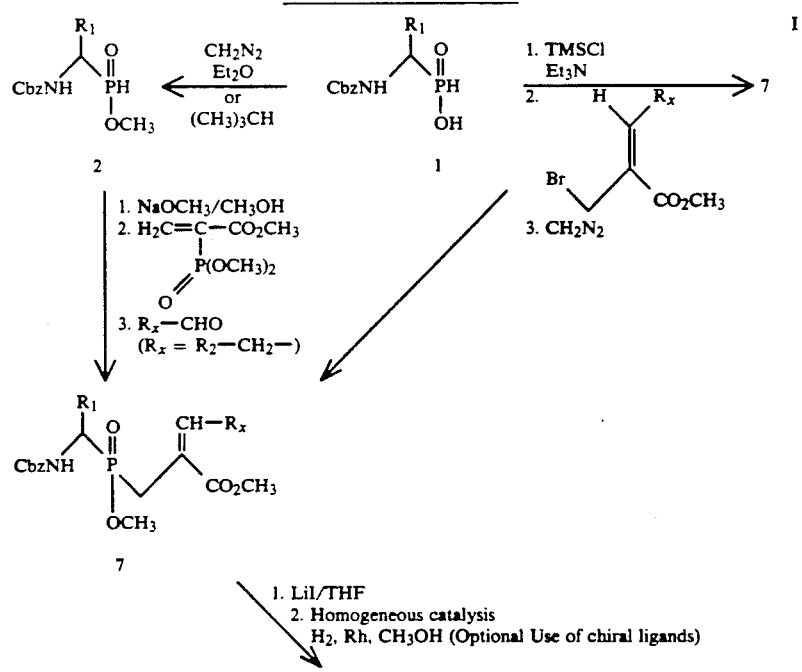

REACTION SCHEME C:

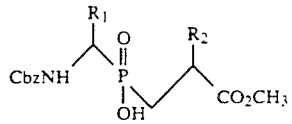

Standard Deprotection
I

This alternative route involves a conjugate addition of the phosphonous ester under the conditions previously outlined to trimethyl-2-phosphonoacrylate. The subsequent anion is then trapped with an aldehyde yielding the dehydro compound as a mixture of E and Z isomers. This same intermediate can be prepared by alkylation of the protected aminoalkylphosphonous acid with substituted 2-bromomethylacrylates under conditions reported by J. K. Thottathil, et al. *Tetrahedron legg.* 25, 4737–40, 4741–44 (19841), hereby incorporated by reference. The olefin may then be selectively reduced using homogenous catalysis. For instance, one may use a $(COD)_2RhCl_2$ complex with an organophosphine ligand in methanol to give compound I which can be further elaborated by procedures already outlined.

Chiral organophosphine ligands such as (−)2,3l-0-isopropylidene-2,3-dihydroxy-1,4-bis (diphenylphosphino)butane, ((−) DIOP), may be used in order to produce the S or R stereoisomers at $R_2$ in high enantiomeric excess.

Preferred diastereomers for antibacterial activity correspond to the absolute stereochemistry of D-Ala-D-Ala at the carbons bearing $R^1$ and $R^2$ and are in general described as D(S), D(R) or S,R-diastereomers and $R_5$ is E or Z.

Preferred diastereomers for dehydropeptidase inhibition correspond to L-amino acids (R stereochemistry) at the carbon bearing $R_1$. Stereochemistry at $R_2$ may correspond to either D- or L-amino acids for good activity (R or S). The stereochemistry at $R_5$ in dehydro analogs can be either E or Z and preferably is Z.

When both antibacterial and dehydropeptidase activities are desired the carbon atom bearing $R_1$ is preferred in the DL-form.

Preferred diastereomers are isolated by chromatography or resolution of intermediates or the end products or their salts.

Racemates may be separated by standard methods including by the use of optically active amines and acids as resolving agents. The following examples are illustrative of the subject invention and should not be construed as being limitations on the scope or input of the instant invention.

EXAMPLE 1

Preparation of
1-Benzyloxycarbonylaminoethylphosphonous acid methyl ester

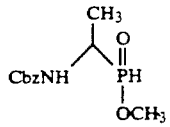

1-Benzyloxycarbonylaminoethylphosphonous acid, prepared by the method of E. K. Baylis et al. [J. Chem. Soc., Perkin Trans, 2845-2853 (1984)] was esterified with diazomethane in an ether solution prepared by a method of F. Arndt [organic Syn. Coll. V. II 165-167 (1943)]. The compound was purified by standard chromatography on silica gel. TLC (silica, 9:1, ethyl acetate:acetonitrile) $R_f=0.51$ NMR (CDCl$_3$, TMS) δ 1.2 and 1.5 (2d, 3H); 2.2 and 10.1 (d, 1H); 3.6 (d, 3H); 3.9 (m, 1H); 5.0 (s, 2H); 6.0–6.6 (overlapping doublets, 1H); 7.2 (s, 5H).

EXAMPLE 2

1-Aminoethyl-[2-carboxy-1-ethylphosphinic acid

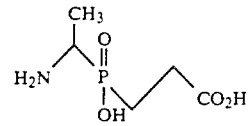

To a stirred solution of 0.36 gm (0.0014 mol) of 1-benzyloxycarbonylaminoethylphosphonous acid methyl ester in 3 ml of methanol at 0° C was added a solution of sodium methoxide in methanol (0.77 ml of a 2N solution) dropwise over 10 minutes whereupon was then added methyl acrylate 0.126 ml (0.0014 mol). The reaction mixture was stirred 30 minutes at 0° C and 4 hours at room temperature whereupon it was diluted with 1N HCl. The mixture was extracted twice with ethyl acetate. The organic fractions were dried over sodium sulfate, filtered through magnesium sulfate and evaporated in vacuo. The product mixture was purified by chromatography (silica, 9:1, ethyl-acetate acetonitrile) to give 0.34 gm of methyl-1-benzyloxycarbonylaminoethyl-[2-carbomethoxy-1-ethyl]-phosphinate.

TLC (silica, 9:1, ethyl acetate:acetonitrile) $R_f=0.47$. NMR (CDCl$_3$) δ 1.4 (m, 3H); 2.00–2.2 (m, 2H); 2.5–2.7 (m, 2H); 3.7 (s, 3H); 3.7–3.9 (m, 3H); 4.1 (quintet, 1H); 5.1 (s, 2H); 5.2 (d, 1/2H); 5.55 (d, ½H); 7.4 (s, 5H).

Elem. Anal. Calc'd for $C_{15}H_{22}NO_6P.\frac{1}{2}H_2O$:
N, 3 64; C, 50.78; H, 6.46;
Found: N, 3.64: C, 50.78; H, 6.46.
Mass spectrum = M$^+$ 343.

5 300 mg of the aforementioned intermediate was subsequently stirred 12 hours in a solution of 30% HBr in acetic acid (5 ml). The reaction mixture was evaporated in vacuo. dissolved in 5 ml of H$_2$O and washed twice with diethylether. The aqueous layer was evaporated vacuo. dissolved in 5 ml of concentrated HCl and stirred 3 days at 50° C and was subsequently evaporated in vacuo. The hydrochloride salt was dissolved in 1 ml of methanol and diluted with 20 ml of propylene oxide. A solid precipitated out which was filtered and washed with ether to give the title compound as a hygroscopic glass. TLC (silica, 1:1:1:1, n-butanol: H$_2$O: acetic acid: ethyl acetate) $R_f=0.28$.

NMR (D$_2$O) δ 1.35–1.5 (2 overlapping d, 3H); 1.85–2.0.

(m, 2H); 2.55-2.65 (ABQ, 2H); 3.25-3.35 (m,1 H).
Elem. Anal. Calc'd for C₅H₁₂NO₄P.½H₂O:
N, 7.19; C, 30.84; H, 6.68;
Found: N, 6.79; C, 30.87; H, 6.70.
Mass spectrum (FAB) M+1, 182.

EXAMPLE 3

1-Aminoethyl-(2-carboxy-1-propyl)phosphinic acid

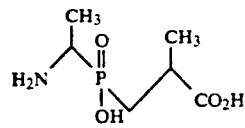

By the same methods used for Example 2 and using methylmethacrylate was made methyl 1-benzyloxycarbonylaminoethyl-[2-carbomethoxy-1-propyl]phosphinate.

NMR (CDCl₃) δ 1.2-1.4 (m, 6H); 1.7-1.9 (m, 1H); 2.2-2.4 (m, 1H); 2.8-2.95 (m, 1H); 3.7(s, 3H); 3.65-3.8 (m, 3H); 4.0-4.2 (m, 1H); 5.15 (s, 2H); 5.4-5.55 (m, 1H); 7.35 s, 5H).

Elem. Anal. Calc'd for C₁₆H₂₄NO₆P:
N, 3.92; C, 53.78; H, 6.72 ;
Found: N, 3.87; C, 53.81; H, 6.47.

The compound was then deprotected by procedures used in Example 2 to provide 1-aminoethyl-(2-carboxy-1-propyl)phosphinic acid.

TLC (silica, 1:1:1:1, n-butanol, water, acetic acid, ethyl acetate) R$_f$=0.4.

NMR (D₂O) δ 1.25 (d, 3H); 1.35-1.45 (overlapping d, 3H); 1.7 -1.9 (m, 1H); 2.1-2.25 (m, 1H); 2.75-2.9 (m, 1H); 3.3-3.45 (m, 1H).

Elem. Anal. Calc'd for C₆H₁₄NO₄P.⅔H₂O:
N, 6.71; C, 34.54; H, 6.76;
Found: N, 6.61; C, 34.84; H, 6.69.

Methyl Carboxyesters

Esters of the carboxylic acid functionality have been made for all the examples and were prepared by dissolving the aminosubstituted alkyl-(2-carboxysubstituted alkyl)phosphinic acid in the appropriate alcohol (methanol if one wants the methyl ester). The solution is then saturated with HCl gas or treated with a few drops of sulfuric acid and then stirred for 24 hours at which time the reaction is evaporated vacuo. The amine salt is then desalted with propylene oxide as in Example 2 to give the carboxyester of the afore described examples.

EXAMPLE 3A

1-Aminoethyl-(2-carbomethoxy-1-propyl)phosphinic acid

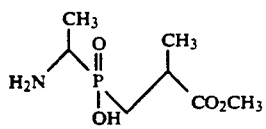

A solution of 100 mg of 1-aminoethyl-(2-carboxy-1 propyl)phosphinic acid in methanol (5 ml) was cooled to 0° C and saturated with HCl gas. The sealed reaction mixture was then stirred 12 hours at room temperature whereupon the methanol was removed vacuo to provide the title compound as a hydrochloride salt which was desalted via the procedure, in Example 2 using propylene oxide to provide the title compound. (80 mg).

NMR (D₂O) δ1.2 (d, 3H); 1.3 (d, 1.5H); 1.5 (d, 1.5H); 1.8-3.0 (m, 3H); 3.3-3.7 (m, 1H); 3.6 (s, 3H).
Mass spectrum (M⁺+1) 210.

EXAMPLE 4

1-Aminoethyl-[2-carboxy-1-n-butylphosphinic acid

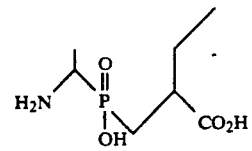

By the methods previously outlined in Example 2 but using methyl-2-ethylacrylate was made methyl-1-benzyloxycarbonylaminoethyl-[2-carbomethoxy-n-butyl] phosphinate.

NMR (CDCl₃) δ 0.8 (overlapping, 3H); 1.2, 1.5 (2d, 3H); 1.4-3.2 (m, 5H); 3.7 (s, 3H); 3.7 (d, 3H); 3.8-4.3 (m, 1H); 5.1 (s, 2H); 5.8 (d, 7.5H); 6.3 (d, 0.5H); 7.3 (s, 5H).

The above compound was deprotected by - 10 aforementioned methods to produce 1-aminoethyl-[2-carboxy-1-n-butyl]phosphinic acid as a hygroscopic glass.

TLC (silica, 1:1:1:1, n-butenol, water, acetic acid, ethyl acetate) R$_f$=0.3.

NMR (D₂O) δ 0.9 (t, 3H); 1.3-1.5 (2, 3H); 1.55-1.8 (m, 3H); 1.95-2.1 (m, H); 1.6-1.75 (m, 1H); 3.2-3.3 (m, 1H).

Elem. Anal. Calc'd for C₇H₁₆No₄P.2H₂O:
N, 6.16; C, 37.00; H, 7.04;
Found: N, 5.95; C, 36.92; H, 7.42.
Mass spectrum: M+H 210.

EXAMPLE 5

1-Aminoethyl-[2-carboxy-1-n-pentylphosphinic acid

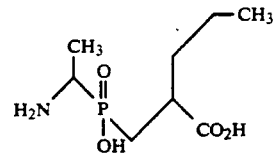

By methods outlined in Example 2 and using methyl-2-propyl acrylate was prepared methyl -benzyl-oxycarbonylaminoethyl-[2-carbomethoxy-1-n-pentyl] phosphinate.

TLC (silica, 9:1, ethyl acetate:acetonitrile) R$_f$=0.45.
NMR (CDCl₃) δ 0.9 (t, 3H); 1.25, 1.5 (2d, 3H); 1.4-3.0 (m, 7H); 3.65 (overlapping s, 3H); 3.7 (d, 3H); 1.6-4.4 (m, 1H); 5.0 (s, 2H); 5.8 (d, .5H); 6.4 (d, 0.5H); 7.3 (s, 5H).

Elem. Anal. Calc'd for C₁₈H₂₈NO₆P.¼H₂O:
N, 3 59; C, 55.45; H, 7.18;
Found: N, 3.66; C, 55.42; H, 7.10.
Mass spectrum M+385.

By the earlier reported methods, the above intermediate was deprotected to produce 1-aminoethyl-carboxy-1-n-pentyl] phosphinic acid.

TLC (silica, 1:1:1:1, n-butanol, H₂O, acetic acid, ethyl acetate) R$_f$=0.4.

NMR (D₂O) δ 1.85 (t, 3H); 1.2-1.5 (m, 7H); 20 1.5-1.9 (m, 4H); 1.9-2.1 (m, 1H); 2.6-2.8 (m, 1H); 3.2-3.35 (m, 1H).

Mass spectrum M-H 222.
Elem. Anal. Calc'd for C₈H₁₈NO₄P.1H₂O:

N, 5.80; C, 39.83; H. 7.46;
Found: N, 5.96; C, 39.48; H, 7.51.

EXAMPLE 6

1-Aminoethyl-[2-carboxy-1-n-hexylphosphinic acid

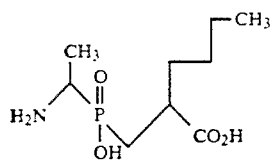

By methods outlined in Example 2 and using methyl-2-n-butyl acrylate was prepared methyl - 1-benzyloxycarbonylaminoethyl-[2-carbomethoxy-1-n-hexyl] phosphinic acid.

TLC (silica, 9:1, ethyl acetate:acetonitrile) $R_f=0.54$
NMR (CDCl$_3$) δ 0.9 (t, 3H); 1.1–3.2 (m, 12H); 3.6 (s, 3H); 3.6 (d, 3H); 3.7–4.3 (m, 1H); 5.0 (s, 2H); 5.5 (d, 0.5H); 5.9 (d, 0.5H); 7.3 (s, 5H).

Mass spectrum M+399.

This intermediate was converted by earlier reported methods to 1-aminoethyl-[2-carboxy-1-n-hexyl] phosphinic acid.

NMR (D$_2$O) δ 1.85 (t, 3H); 1.15–1.50 (m, 7H); 1.55–1.8 (m, 3H); 1.95–2.1 (m, 1H); 2.6–2.8 (m, 1H); 3.15–3.3 (m, 1H).

Elem. Anal. Calc'd for C$_9$H$_{20}$NO$_4$P.$\frac{1}{2}$H$_2$O:
N, 5.79; C, 44.72; H, 8.28;
Found: N, 5.75; C, 44.40; H, 8.08.
Mass spectrum M+238.

EXAMPLE 7

1-Aminoethyl-[2-carboxy-4-methyl-1-n-pentyl]phosphinic acid

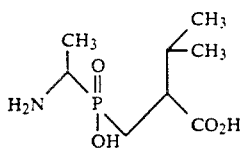

By methods outlined in Example 2 and using methyl-2-isobutyl acrylate was made methyl-1-benzyloxycarbonylaminoethyl-[2-carbomethoxy-4-methyl-1-n-pentyl] phosphinate.

NMR (D$_2$O) 1.9 (overlapping d, H); 1.5–3.2 (m, 9H); 4.6 (d, 3H); 3.8–4.3 (m, 1H); 5.1 (s, 2H); 5.5 (d, 0.5H); 5.9 (d, 0.5H); 7.2 (s, 5H).

Elem. Anal. Calc'd for C$_{19}$H$_{30}$NO$_6$P.$\frac{1}{4}$H$_2$O:
N, 3.46; C, 56.51; H, 7.44;
Found: N, 3.56; C, 56.34; H, 7.47,
Mass spectrum M+400.

The intermediate was converted to 1-aminoethyl-[2-carboxy-4-methyl-1-n-pentyl] phosphinic acid by methods reported in Example 2.

NMR (CDCl$_3$) δ 1.9 (overlapping d, 6H); 1.3–1.65 (m, 6H); 1.75 (overlapping t, 1H); 1.9–2.1 (m, 1H); 2.7–2.9 (m, 1H); 3.15–3.35 (m, 1H).

Elem. Anal. Calc'd for C$_9$H$_{20}$NO$_4$P.1H$_2$O:
N, 5.49; C, 42.35; H, 7.84;
Found: N, 5.55; C, 42.79; H, 8.03.
Mass spectrum M−236.

EXAMPLE 8

1-Aminoethyl-[2-carboxy-5-cyclohexyl-1-n-pentyl]-phosphinic acid

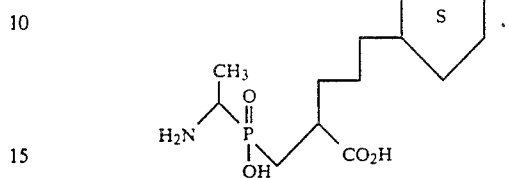

By methods outlined in Example 2 and using methyl-2-[3-cyclohexyl-1-propyl]acrylate was prepared methyl-1-benzyloxycarbonylaminoethyl-[2-carbomethoxy-cyclohexyl-1-n-pentyl] phosphinate.

NMR (CDCl$_3$) δ 0.8–3.1 (m, 23H); 3.6 (s, 3H); 3.6 (d, 3H); 3.6–4.2 (m, 1H); 5.0 (s, 2H); 5.2 (d, 0.5H); 5.5 (c, 0.5H); 7.2 (s, 5H).

Elem. Anal. Calc'd for C$_{24}$H$_{38}$NO$_6$P:
N, 3.00; C, 61.66; H, 8.19;
Found: N, 3.19; C, 61.32; H, 8.08.
Mass spectrum M+468.

This compound was converted by methods in Example 2 to 1-aminoethyl-[2-carboxy-5-cyclohexyl-1-n-pentyl]phosphinic acid.

TLC (silica, 1:1:1:1, n-butanol: H$_2$O: acetic acid: ethyl acetate) $R_f=0.66$.

NMR (D$_2$O) δ 0.8–3.2 (m, 23H); 3.7–4.2 (m, 1H).
Mass spectrum M+304.

EXAMPLE 9

1-Aminoethyl-[2-carboxy-1-nonvylphosphinic acid

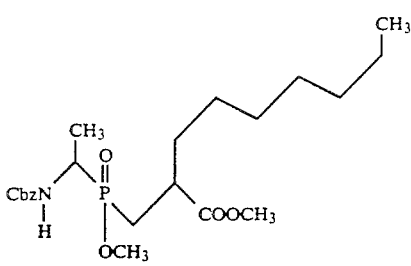

Methyl-1-Benzyloxycarbonylaminoethyl-[2-carbomethoxy-1-nonyl] phosphinate was prepared in 60% yield by the method described in Example 2.

NMR (CDCl$_3$, 300 MHz: δ 0.9 (m, 3H); 1.2–1.4 (m, H); 1.6 (m, 2H); 1.8 (m, 1H); 2.2 (m, 1H); 2.8 (m, 1H); 3.7 (m, 6H); 4.1 (m, 1H); 5.0–5.3 (m, 3H); 7.4 (br s, 5H).

Elem. Anal. Calc'd for C$_{22}$H$_{36}$NO$_6$P:
N, 3.17; C, 59.85; H, 8.22;
Found: N, 3.06; C, 59.94; H, 8.03.
Mass spectrum (pos. ion FAB): M+H 442 (100%)
Analytical TLC: $R_f=69$ (ethyl acetate/acetonitrile/methanol, 9:1:.5).

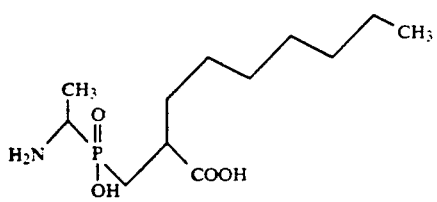

The title compound was prepared by the procedure described in Example 2.

NMR (D$_2$O, 300 MHz): δ 0.8 t, 3H); 1.3-1.5 (m, 13H); 1.5-1.8 (m, 3H); 2.0 (m, 1H); 2.7 (m, 1H); 3.2 (m, 1H).

Elem. Anal. Calc'd for C$_{12}$H$_{26}$NO$_4$P:
N, 5.01; C, 51.60; H, 9.38;
Found: N, 5.03; C, 50.94; H, 9.02.

Mass spectrum (pos. ion FAB): M+H 280 (100%).

Analytical TLC: R$_f$=0.67 (ethyl acetate/1-butanol/acetic acid/water, 1:1:1:1).

EXAMPLE 10

1-Aminoethyl-[2-carboxy-3-phenyl-1-n-propyl]-phosphinic acid

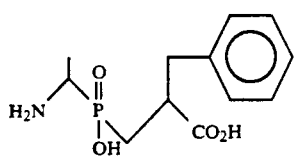

By methods used in Example 2 and employing methyl-2-benzylacrylate was made methyl-1-benzyloxycarbonylaminoethyl-[2-carbomethoxy-3-phenyl-1-n-propyl]phosphinate.

TLC (silica, 9:1, ethyl acetate:acetonitrile) R$_f$=0.61,
NMR (CDCl$_3$) δ 1.1-1.5 (2d, 3H); 1.7-3.1 (m, 5H); 3.4-3.6 (m, 6H); 3.7-4.3 (m, 1H); 5.0 s, 2H); 5.6 d, 0.5H); 6.1 (d, 0.5H); 7.0 (bs, 5H); 7.2 s, 5H).

Elem. Anal. Calc'd for C$_{22}$H$_{28}$NO$_6$P.¼H$_2$O:
N, 3.20; C, 60.34; H, 6.44;
Found: N, 2.78; C, 60.17; H, 6.54.

Mass spectrum M+433.

This compound was converted by methods in Example 2 to 1-aminoethyl-[2-carboxy-3-phenyl-1-n-propyl]-phosphinic acid.

TLC (silica, 1:1:1:1, n-butanol:H$_2$O:acetic acid: ethyl acetate) R$_f$=0.42.

NMR (D$_2$O) δ 1.25-1.45 (m, 3H); 1.7-1.9 (m, 1H); 2.0-2.15 (m, 1H); 2.8-3.1 (m, 3H); 3.1-3.3 (m, 1H); 7.2-7.45 (2 overlapping s, 10H).

Elem. Anal. Calc'd for C$_{12}$H$_{18}$NO$_4$P.1H$_2$O:
N, 4.84; C, 49.82; H, 6.22;
Found: N, 4.61; C, 49.45; H, 6.32.

Mass spectrum M-1 270.

EXAMPLE 11

1-Aminoethyl-[2-carboxy-3-phenyl-1-n-butyl]-phosphinic acid

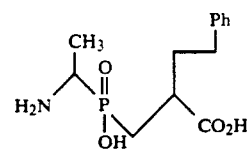

By methods used in Example 2 and employing methyl-2-phenethylacrylate was made methyl-1-benzyloxycarbonylaminoethyl-[2-carbomethoxy-4-phenyl-1-n-butyl]-phosphinate.

TLC (silica, 9:1, ethyl acetate:acetonitrile) R$_f$=0.57.
NMR (CDCl$_3$) δ 1.2 d, 1.5H); 1.5 (d, 1.5H); 1.6-3.1 (m, 7H); 3.6 (s, 3H); 3.6 (d, 3H); 3.7-4.3 (m, 1H); 5.0 s, 2H); 5.4 (d, .5H); 5.9 (d, .5H); 7.1 (s, 5H); 7.3 (s, 5H).

Mass spectrum: M+1 448.

This compound was converted by methods in Example 2 to 1-aminoethyl-[2-carboxy-4-phenyl-1-n-butyl]-phosphinic acid.

TLC (silica, 1:1:1:1, n-butanol: H$_2$O: acetic acid: ethyl acetate) R$_f$=0.30.

NMR (D$_2$O) δ 1.35-1.5 (overlapping d, 8H); 1.85-2.05 (m, 3H); 2.1-2.3 (m, 1H); 3.3-3.45 (m, 8H); 7.2-7 45 μm, 10H).

Elem. Anal. Calc'd for C$_{13}$H$_{20}$NO$_4$P.¼H$_2$O:
N, 4.83; C, 53.88; H, 6.90;
Found: N, 4.62; C, 53.78; H, 7.19.

Mass spectrum M+−1 284.

EXAMPLE 12

1-Aminoethyl-[2-carboxy-5-phenyl-1-n-pentyl]-phosphinic acid

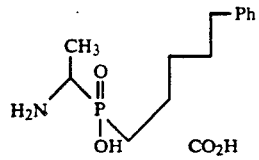

By methods used in Example 2 and employing methyl-2-(3-phenyl-1-propyl)acrylate was prepared methyl-1-benzyloxycarbonylaminoethyl-[2-carbomethoxy-phenyl-1-n-pentyl]Phosphinate.

TLC (silica, 9:1, ethyl acetate:acetonitrile) R$_f$=0.44.
NMR (CDCl$_3$) δ 1 .2 (d, 1.5H); 1.5 (d, 1.5H); 1.5-3.2 (m, 9H); 3.6 (d, 3H); 3.7 (s, 3H); 3.7-4.2 (m, 1H); 5.0 (s, 2H); 5.5 (d, 0.5H); 5.9 (d, .5H); 7.1 s, 5H); 7.3 (s, 5H).

This compound was converted by methods in Example 2 to 1-aminoethyl-[2-carboxy-5-phenyl-1-n-pentyl]-Phosphinic acid.

TLC (silica, 1:1:1:1, n-butanol: H$_2$O: acetic acid: ethyl acetate) R$_f$=0.32.

NMR (D$_2$O) δ 1.3-1.4 (2 overlapping d, 3H); 1.4-1.7 (m, 5H); 1.85-2.0 (m, 1H); 2.1-2.3 (m, 1H); 2.45-2.6 (m, 1H); 2.6-2.8 (m, 1H); 3.45-3.55 (m, 1H); 7.1-7.3 (m, 10H).

Mass spectrum: (M+1) 266.

Elem. Anal. Calc'd for C$_{14}$H$_{22}$NO$_4$P.1.5H$_2$O:
N, 4.413 C, 51.53; H, 7.66;
Found: N, 4.04; C, 51.35; H, 7.41.

EXAMPLE 13

1-Aminoethyl-[2,3-dicarboxy-1-n-propyl] phosphinic acid

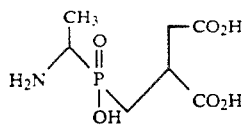

By methods used in Example 2 and employing methyl-2-t-butoxycarbonylmethylacrylate was prepared methyl-1-benzyloxycarbonylaminoethyl-[2-carbomethoxy-3-butoxycarbonyl-1-propyl]phosphinate.

TLC (silica, 1, ethyl acetate:acetonitrile) $R_f=0.58$.

NMR (CDCl$_3$) δ 1.2 (d, 1.5H); 1.5 (d, 1.5H); 1.4 (s, 9H); 1.8–3.2 (m, 5H); 1.625 (s, 3H); 1.64 (d, H); 1.8–3.3 (m, 1H); 5.05 s, 2H); 5.3 (d, 0.5H); 5.7 (d, 0.5H); 7.2 s, 5H).

Elem. Anal. Calc'd for $C_{21}H_{32}NO_8P \cdot \frac{1}{4}H_2O$:
N, 3.03; C, 54.60; H, 6.98;
Found: N, 3.15; C, 54.65; H, 6.94.

Mass spectrum $M^+457$.

This compound was converted by methods in Example 2 to 1-aminoethyl-[2,3-dicarboxy-1-n-propyl]Phosphinic acid.

NMR (D$_2$O) δ 1.3 (d, 1.5H); 1.55 (d, 1.5H); 1.8–2.4 (m, 2H); 2.6–2.8 (m, 2H); 2.9–3.7 (m, 3H).

Mass spectrum: $(M^+ - 1)$ 238.

EXAMPLE 14

1-Aminoethyl-[2,5-dicarboxy-1-n-pentyl]phosphinic acid

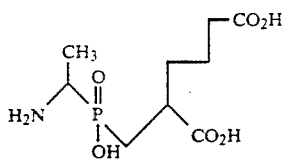

By methods used in Example 2 and employing dimethyl-2-(3-carboxy-1-propyl)acrylate was prepared trimethyl-1-benzyloxycarbonylaminoethyl-[2,5-dicarboxy-n-pentyl]phosphinate.

TLC (silica, 9:1, ethyl acetate:acetonitrile) $R_f=0.48$.

NMR (CDCl$_3$) δ 1.2–3.1 (m, 12H); 3.55 (s, 3H); 3.6 (d, 3H); 3.7–4.2 (m, 1H); 5.0 (s, 2H); 5.3 (d, 0.5H); 5.75 (d, 0.5H), 7.2 (s. 5H)

Mass spectrum: $M^+443$.

This compound was converted by methods in Example 2 to 1-aminoethyl-[2,5-dicarboxy-1-n-propyl]phosphinic acid.

NMR (D$_2$O) δ 1.1–2.8 (m, 12H); 3.1–3.6 (m, 1H).

Mass spectrum: $(M^+ + 1)$ 268.

EXAMPLE 15

1-Aminoethyl-[2-carboxy-6-hydroxy-1-n-hexyl]phosphinic acid

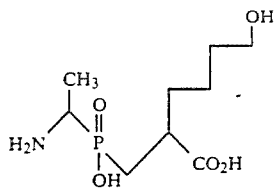

By methods used in Example 2 and employing methyl-2-[4-t-butyldimethylsilyloxy-1-n-butyl]acrylate was prepared methyl-1-benzyloxycarbonylaminoethyl-carboxy-6-t-butyldimethylsilyloxy-1-n-butyl]phosphinate.

TLC (silica, 9:1, ethyl acetate:acetonitrile) $R_f=0.59$.

NMR (CDCl$_3$) δ 0.0 (s, 6H); 0.9 (s, 9H); 1.1–3.2 (m, 12H); 1.4–1.7 (m, 9H); 1.7–4.3 (m, 1H); 5.0 (s, H); 5.4 (d, 0.5H); 5.8 (d, 6H); 7.2 (s, 5H).

Mass spectrum: $M^+529$.

This compound was converted by methods in Example 2 to 1-aminoethyl-[2-carboxy-6-hydroxy-1-n-hexyl] phosphinic acid.

NMR (D$_2$O) δ 1.15–3.2 (m, 12H): 3.25–3.65 (m, 3H).

Mass spectrum: $(M^+ + 1)$ 264.

EXAMPLE 16

1-Aminoethyl-[2-carboxy-4-(1-naphthyl)-1-n-butyl]-phosphinic acid

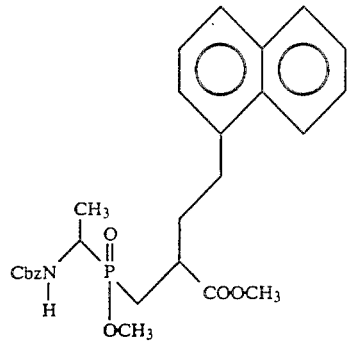

Methyl-1-benzyloxycarbonylaminoethyl-[2-carbomethoxy-4-(1-naphthyl)-1-n-butyl] phosphinate was prepared in 65% yield by the method described in Example 2.

NMR (CDCl$_3$, 300 MHz): δ 1.4 (q, 3H); 1.9–2.2 (m, H); 2.3 (m, 1H); 3.0 (m, 3H); 3.7 (m, 6H); 4.1 (m, 1H); 5.1 (m, 3H); 7.2–8 0 (m, 12H).

Elem. Anal. Calc'd for $C_{27}H_{32}NO_6P \cdot \frac{1}{2}H_2O$:
N, 2.76; C, 63.96; H, 6.51;
Found: N, 2.42; C, 63.85; H, 6.33.

Mass spectrum (EI): $M^+497$ (10%).

Analytical TLC $R_f=0.58$ (ethyl acetate/acetonitrile/methanol 9:1:.5).

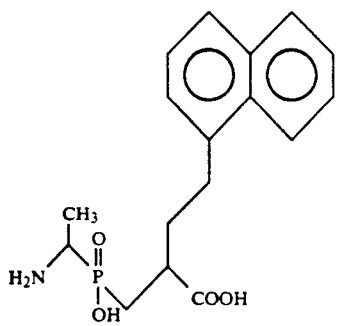

The title compound was prepared by the procedure described in Example 2.

NMR (D$_2$O, 300 MHz): δ 1.4 (q, 3H); 1.8 (m, 1H); 2.1 (m, 3H); 2.8 (m, 1H); 3.1 (m, 3H); 7.4–8.1 (m, 7H).

Elem. Anal. Calc'd for C$_{17}$H$_{23}$NO$_4$P.3/2H$_2$O:

N, 3.86; C, 56.30; H, 6.90;

Found: N, 3.66; C, 56.23; H, 6.71.

Mass spectrum (neg. ion FAB): M-H 334 (25%).

Analytical TLC: R$_f$=0.67 (ethyl acetate/1-butanol-/acetic acid/water 1:1:1:1).

EXAMPLE 17

1-Aminoethyl-[2-carboxy-4-(2-naphthyl)-1-n-butyl]-phosphinic acid

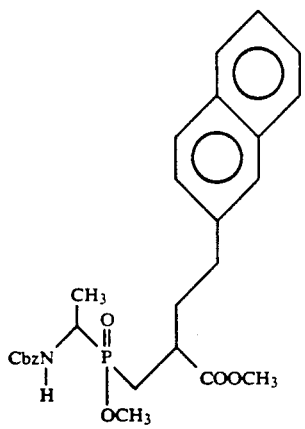

Methyl-1-benzyloxycarbonylaminoethyl-[2-carbomethoxy-4-(2-naphthyl)-1-n-butyl]phosphinate was prepared in 75% yield by the method described in Example 2.

NMR (CDCl$_3$, 300 MHz : δ 1.4 (m, 3H); 1.8–2.1 (m, 3H); 2.3 (m, 1H); 2.7 (m, 2H); 2.9 (m, 1H); 3.6–3.7 (m, 6H); 4.1 (m, 1H); 5.1–5.3 (m, 3H); 7.3–7.8 (m, 12H).

Elem. Anal Calc'd for C$_{27}$H$_{32}$NO$_6$P.½H$_2$O:

N, 2.76; C, 63.96; H, 6.51;

Found: N, 2.40; C, 63.79; H, 6.43.

Mass spectrum (EI): M$^+$497 (12%).

Analytical TLC: R$_f$=0.67 (ethyl acetate/acetonitrile/methanol 9:1:.5).

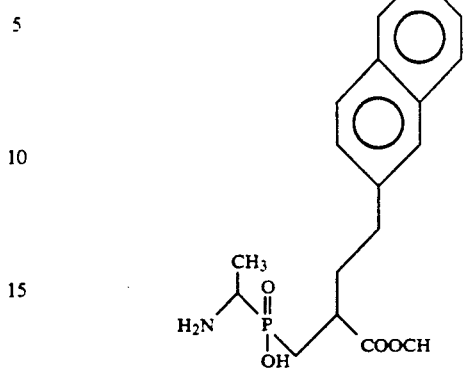

The title compound was prepared by the procedure described in Example 2.

NMR (D$_2$O, 300 MHz): δ 1.3 (q, 3H); 1.8 (m, 1H); 2.1 (m, 3H); 2.8 (m, 3H); 3.2 (m, 1H); 7.4–7.9 (m, 7H). Mass spectrum (pos. ion FAB): M+H 336 (100%).

Analytical TLC: R$_f$=0.65 (ethyl acetate/1-butanol-/acetic acid/water 1:1:1:1).

EXAMPLE 18

1-Aminoethyl-[2-carboxy-5-(4-pyridyl)-1-n-pentyl]-phosphinic acid

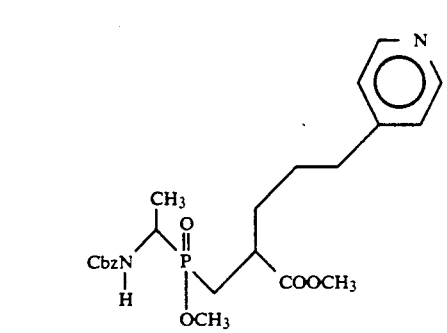

Methyl-1-benzyloxycarbonylaminoethyl-[2-carbomethoxy-5-(4-pyridyl)-1-n-pentyl]phosphinate was prepared in 84% yield by the method described in Example 2.

NMR (CDCl$_3$, 300 MHz): δ 1.35 q, 3H); 1.80 (m, 1H); 2.25 (m, 1H); 2.55 (m, 1H); 2.6 (m, 5H); 2.80 (m, 1H); 3.6 (d, 3H); 3.7 (s, 3H); 4.1 (m, 1H); 5.1 (d, 12Hz,0.5H); 5.1 (s, 2H); 5.7 (d, 12Hz, .5H); 7.1 (d, 6Hz, 2H); 7.35 (br s, 5H); 8.5 (d, 6Hz, 2H).

Elem. Anal. Calc'd for C$_{23}$H$_{31}$N$_2$O$_6$P:

N, 6.06; C, 59.73; H, 6.76;

Found: N, 5.99; C, 59.08; H, 6.73.

Mass spectrum (pos. ion FAB): M+H 463 (100%).

Analytical TLC: R$_f$=0.30 (ethyl acetate/acetonitrile/methanol 9:1:.5).

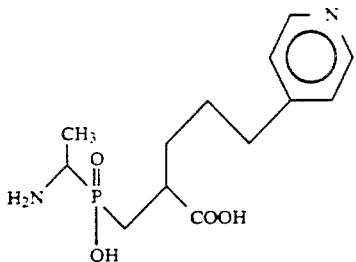

The title compound was prepared from the above compound by the methods described previously. NMR (D$_2$O, 300 MHz): δ 1.3 (q, 3H); 1.7 (m, 5H); 2.1 (m, 1H); 2 8 (m, 1H); 3.0 (m, 2H); 3.2 (m, 1H); 7.9 (d, 8Hz, 2H); 8.6 (d, 8Hz, 2H).

Mass spectrum (pos. ion FAB): M+H 301 (100%).

Analytical TLC: R$_f$=0.15 (ethyl acetate/1-butanol-/acetic acid/water, 1:1:1:1).

EXAMPLE 19

1-L-Aminoethyl-(2-carboxy-1-propyl)phosphinic acid

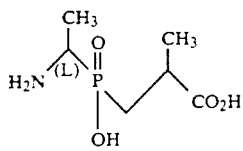

By the same methods used for Example 2, but methyl ester and methyl methacrylate, was made methyl-1-benzyloxycarbonyl-L-aminoethyl-[2-carbomethoxy-1-propyl]phosphinate.

TLC: (silica, 9:1, ethylacetate:acetonitrile) R$_f$=0.54.

NMR (CDCl$_3$): δ 1.2-1.5 (m, 6H); 1.7-1.9 (m, 1H); 2.2-2.4 (m, 1H); 2.8-3.0 (m, 1H); 3.7 (s, 3H); 3.6-3.8 (d, 3H); 4.0-4.2 (m, 1H); 5.1 (s, 2H); 5.2-5.4 (m, 1H); 7.3 (s, 5H).

Elem. Anal. Calc'd for C$_{16}$H$_{24}$NO$_6$Pl.½H$_2$O:
N, 3.82; C, 52.45; H, 6.60;
Found: N, 3.98, C, 52.76; H, 6.55.

Mass spectrum: FAB (M+H)=359.

The compound was deprotected by procedures used in Example 2 to provide 1-L-aminoethyl-(2-carboxy-1-propyl)phosphinic acid.

TLC: (silica, 1:1:1:1, n-butanol, water, acetic acid, ethyl acetate) R$_f$=0.52.

NMR (D$_2$O): δ 1.25 (t, 3H); 1.3-1.5 (overlapping d, 3H); 1.7-1.9 (m, 1H); 2.1-2.3 (m, 1H); 2.75-2.9 (m, 1H); 3.3-3.5 (m, 1H).

Elem. Anal. Calc'd for C$_6$H$_{14}$NO$_4$P.1H$_2$O: N, 6.57; C, 33.81; H, 6.62;
Found: N, 6.51; C, 33.63; H, 6.39.

Mass spectrum: FAB (M+H)=196.

EXAMPLE 20

1-D-Aminoethyl-(2l-carboxy-1-propyl)phosphinic acid

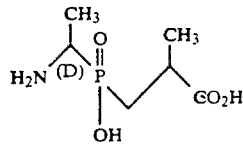

By the same method used for Example 2, but using 1-(D)-benzyloxycarbonylaminoethylphosphous acid methyl methacrylate, was made methyl-1-benzyloxycarbonyl-D-aminoethyl-[2-carbomethoxy-1-propyl]-phosphinate.

TLC: (silica, 9:1, ethylacetate:acetonitrile) R$_f$=0.54.

Rotation data: $a_D = \frac{(+0.177)(10)}{0.0475} = +37.2°$

XL 300 NMR: δ 1.15-1.45 (m, 6H); 17-1.9 (m, 1H); 2.2-2.4 (m, 1H); 2.8-3.0 (m, 1H); 3.7 (s, 3H); 3.55-3.8 (m, 3H); 4.0-4.2 (m, 1H); 4.95-5.1 (m, 1H); 5.1 (s, 2H); 7.4 (s, 5H).

El. analysis: Calc. for C$_{16}$H$_{24}$NO$_6$P.½H$_2$O:
N, 3.82; C, 52.46; H, 6.60;
Found: N, 4.04; C, 52.02; H, 6.50.

Mass Spectrum: FAB (m+H)=358.

The compound was deprotected by procedures used in Example 2 to provide 1-D-aminoethyl-(2-carboxy-1l-propyl)phosphinic acid.

TLC: (silica, 1:1:1:1, n-butanol, water, acetic acid, ethyl acetate) R$_f$=0.64.

NMR (D$_2$O): δ 1.2 (d, 3H); 1.3-1.4 (2d, 3H); 1.65-1.8 (m, 1H) 2.05-2.2 (m, 1H); 2.7-2.9 (m, 1H); 3.25-3.4 (m, 1H);

El. Analysis: Calc. for C$_6$H$_{14}$NO$_4$P.¼H$_2$O:
N, 7.01; C, 36.10; H, 7.07;
Found: N, 6.70; C, 36.05; H, 6.99.

Mass Spectrum: FAB (m+H)=196, (2m+H)=391.

EXAMPLE 21

1-L-Aminoethyl-(2-carboxy-1-n-butyl)phosphinic acid

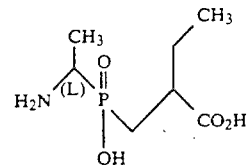

By the same methods used for Example 2, but using 1-(L)-benzyloxyaminoethylphosphorous acid methyl ester and methyl-2-ethacrylate, was made methyl-1-benzyloxycarbonyl-L-aminoethyl-[2-carbomethoxy-1-n-butyl]phosphinate.

TLC: (silica, 9:1, ethyolacetate:acetonitrile) R$_f$=0.54;

XL 300 NMR (CDCl$_3$): δ 0.8-1.0 (m, 3H); 1.2-1.45 (m, 3H); 1.5-1.7 (m, 2H); 1.15-1.9 (m, 1H); 2.15-2.35 (m, 1H); 3.65-3.85 (m, 1H); 3.7 (s, 3H); 3.6-3.8 (m, 3H); 4.0-4.2 (m, 1H); 5.1 (s, 2H); 5.3-5.5 (m, 1H); 7.35 (s, 5H).

El. analysis: Calc. for C$_{17}$H$_{26}$NO$_6$P.½H$_2$O:
N, 3.68; C, 53.68; H, 6.89;
Found: N, 4.00; C, 53.80; H, 6.70.

Mass Spectrum: FAB (m+H)=372.

Rotation data: $a_D = \frac{(+0.006)(10)}{0.0127} = +4.72°$

The compound was deprotected by procedures used in Example 2 to provide 1-L-aminoethyl-(2-carboxy-1-n-butyl)phosphinic acid.

TLC: (silica, 1:1:1:1, n-butanol, water, acetic acid, ethyl acetate) R$_f$=0.57.

NMR (D$_2$O): δ0.85 (t, 3H); 1.3-1.45 (2d, 3H; 1.55-1.7 (m, 2H); 1.75-1.8 (m, 1H); 2.05-2.2 (m, 1H); 2.6-2.75 (m, 1H); 3.3-3.4 (m, 1H).

El. analysis: Calc. for $C_{17}H_{16}NO_4P \cdot \frac{1}{2}H_2O$:
N, 5.71; C, 34.29; H, 6.58;
Found: N, 5.74; C, 34.36; H, 6.51.
Mass spectrum: FAB (m+H)=210.

EXAMPLE 22

1-D-Aminoethyl-(2l-carboxy-1-n-butyl)phosphinic acid

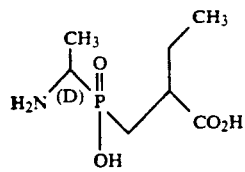

By the methods previously described in Example 2, but using 1-(D)-benzyloxyaminoethylphosphonous acid methylester and methyl-2-ethylsulfate, was made methyl-1-benzyloxycarbonyl-D-aminoethyl-[2-carbomethoxy-1l-n-butyl]phosphinate.

TLC: (silica, 9:1, ethylacetate:acetonitrile) $R_f=0.58$.
NMR(CDCl$_3$): δ 0.7-1.1 (m, 3H); 1.1-2.4 (m, 7H); 3.7 (s, 3H); 3.6-3.8 (d, 3H); 3.9-4.3 (m, 1H); 5.1 (s, 2H); 5.9 (d, 1/2 H); 6.4 d, 1/2 H); 7.2 (brs, 5H).

El. analysis: Calc. for $C_{17}H_{26}NO_6P \cdot \frac{1}{2}H_2O$:
N, 3.68; C, 53.68; H, 6.89;
Found: N, 3.81; C, 53.63; H, 6.51.
Mass Spectrum: FAB (m+H)=372.

Rotation data: $\alpha_D = \frac{(+0.119)(10)}{0.0434} = +276.4°$

The compound was deprotected by procedures used in Example 2 to provide 1-D-aminoethyl-(2-carboxy-1-n-butyl)phosphinic acid.

TLC: (silica, 1:1:1:1, n-butanol, water, acetic acid, ethyl acetate) $R_f=0.46$.

XL 300 NMR (D$_2$O): δ 0.85 (overlapping t, 3H); 1.3-1.4 (overlapping d, 3H); 2.55-2.7 (m, 2H); 2.75-2.9 (m, 1H); 2.05-2.2 (m, 1H); 2.6-2.85 (m, 1H); 3.3-3.4 (m, 1H).

El. analysis: Calc. for $C_7H_{16}NO_4P \cdot 11/4 H_2O$:
N, 6.04; C, 36.29; H, 6.96;
Found: N, 6.07; C, 36.40; H, 7.27.
Mass Spectrum: FAB (m+H)=210 (2m+H)=419.

EXAMPLE 23

1-L-Aminoethyl-2-carboxy-1-nonyl1-phosphinic acid

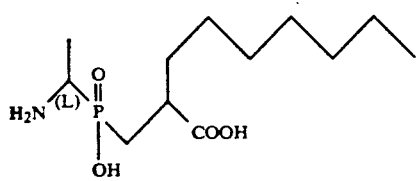

The title compound was made from methyl 2-n-heptylpropenoate following the general procedure of Example 19. Spectral data of the obtained compound:

| NMR (300 MHz, D$_2$O): δ | |
|---|---|
| 3.2(m, 1H) | 1.6(br s, 2H) |
| 2.7(m, 1H) | 1.4(q, 3H) |
| 2.0(m, 1H) | 1.2(br s, 10H) |
| 1.7(m, 1H) | 0.8(t, 3H) |

| Mass Spec (neg. ion FAB): | |
|---|---|
| 278 (M − H, 100%) | |
| Elemental analysis: | |
| calc. for $C_{12}H_{26}NO_4P$ | found |
| C: 51.60 | 51.53 |
| H: 9.38 | 9.07 |
| N: 5.01 | 4.78 |

EXAMPLE 24

1-D-Aminoethyl-[2-carboxy-1-nonyl]-phosphinic acid

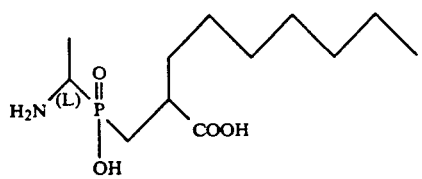

The compound was made from methyl 2-n-heptylpropenoate following the general procedure of Example 20.

| NMR (300 MHz, D$_2$O): | |
|---|---|
| 3.2(m, 1H) | 1.6(br s, 2H) |
| 2.7(m, 1H) | 1.4(q, 3H) |
| 2.0(m, 1H) | 1.2(br s, 10H) |
| 1.7(m, 1H) | 0.8(t, 3H) |

| Mass Spec (neg. ion FAB): | |
|---|---|
| 278 (M − H, 100%) | |
| Elemental analysis: | |
| calc. for $C_{12}H_{26}NO_4P$ | found |
| C: 51.60 | 50.97 |
| H: 9.38 | 9.04 |
| N: 5.01 | 5.02 |

EXAMPLE 25

A. [1-(Benzoxycarbonylamino)ethyl](2-methoxycarbonyl-2-propenyl)-phosphinic acid

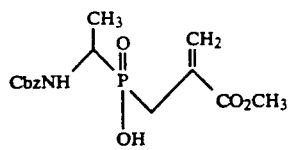

To a stirred solution of 2.25 g (9.3 mmol) of 1-(benzyloxycarbonylamino)ethylphosphonous acid in 70 ml of methylene chloride, were added triethylamine (2.87 ml, 20 mmol), trimethylsilyl chloride (2.60 ml, 20 mmol), and methyl 2-bromomethylacrylate (1.66 g, 9.3 mmol) at 0° C. After stirring at room temperature for 20 hours, the reaction mixture was washed with H$_2$O, 2N HCl, and then saturated NaCl solution and dried over anhydrous magnesium sulfate. The mixture obtained by filtration and evaporation was purified by silica gel chromatography (eluted with chloroform followed by 10% methanol-chloroform) to give 2.50 g (yield 79%) of the product.

NMR (CDCl$_3$, δ) δ 1.4 (m, 3H), 2.9 (m, 2H), 3.75 (s, 3H), 4.2 (m, 1H), 5.10 (s, 2H), 5.60 (d, 1H), 5.85 (m, 1H), 6.30 (m, 1H), 7.30 (s, 5H).

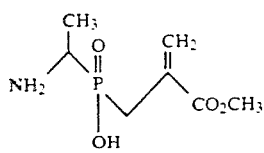

B. (1-Aminoethyl)(2-carboxy-2-propenyl)phosphinic acid)

To a solution of 341 mg (1 mmol) of 1-(benzyloxycarbonylamino)-ethyl](2-methoxycarbonyl-2-propenyl)-phosphinic acid in methanol (20 ml) and H₂O (8 ml), was 1N NaOH (2.2 ml, 2.2. mmol) and the mixture was refluxed for 3 hours. After evaporation of methanol, the aqueous layer was washed with chloroform twice and then acidified with 2N HCl. The aqueous solution was extracted with chloroform four times and the combined organic layer was dried over anhydrous magnesium sulfate. Filtration followed by evaporation gave 330 mg (yield 100%) of [1-(benzyloxycarbonylamino)ethyl](2-carboxy-2-propenyl)phosphinic acid. The obtained above phosphinic acid (163 mg, 0.5 mmol) and sodium iodide (300 mg, 2 mmol) were dissolved in acetonitrile (3 ml). Then trimethylsilyl chloride (0.25 ml) was added and the mixture was stirred at room temperature for 6 hours. H₂O was added and the mixture was washed with chloroform eight times and adjusted at pH 4 by the addition of saturated sodium carbonate solution. After evaporation to dryness, ethyl acetate (10 ml) was added and the precipitate was filtered. It was dissolved in methanol (10 ml) and the insoluble material was filtered off. Methanol was evaporated and the residue was purified by reversed-phase column chromatography (C-18, eluted with H₂O) to give 60 mg (yield 62%) of (1-aminoethyl)(2-Carboxy-2-propenyl)phosphinic acid.

TLC (silica, butanol:acetic acid:H₂O=4:1:2) $R_f$=0.15.

NMR (CD₃OD, ) 1.4 (m, 3H), 2.8 (m, 2H), 5.4 (m, 1H), 5.9 (m, 1H).

EXAMPLE 26

(1-Aminoethyl)(2-carboxy-3-bromopropyl)phosphinic acid

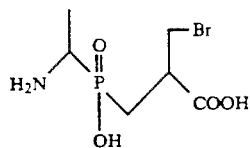

A mixture of [1-(benzyloxycarbonylamino)ethyl](2-carboxy-2-propenyl)phosphinic acid (330 mg, mmol) in 30% hydrogen bromide containing acetic acid solution was stirred at room temperature for 4.5 hours. After ether (20 ml) was added, the precipitate was filtered and washed thoroughly with ether, and then it was dissolved in 2 ml of methanol. The colorless powder, which was obtained by the addition of 20 ml of propylene oxide, was filtered and washed with ether to afford 145 mg (yield 53%) of (1-aminoethyl)(2-carboxy-3-bromo-propyl)phosphinic TLC (silica, butanol:acetic acid:H₂O=4:1:2) $R_f$=0.20.

NMR (CD₃OD,300MHz) 1.4 (m, 3H), 2.1 (m, 2H), 3.3 (m, 1H), 3.7 (m, 1H).

EXAMPLE 27

Methyl-(1-carbobenzyloxyaminoethyl)-(2-carbomethoxy-2-propenyl)-phosphinate

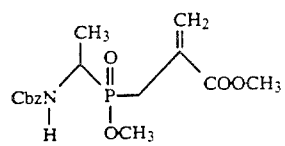

A solution of 1.053 g (4.097 mmol) phosphinate ester (synthesized according to the Procedure given in Example 1) in 2.5 mL distilled methanol at 0° was treated dropwise over 10 minutes with 2.25 mL of 2.0N methanolic sodium methoxide (4.50 mmol; 1.1 eq.). When the addition of base was complete, the mixtures was stirred an additional 5 minutes at 0° before a solution of 0.96 ml (1.20 g, 6.2 mmol, 1.5 e.g.) trimethyl-2-phosphonoacrylate (Fluka) in 1 ml distilled methanol was added dropwise over 5 minutes. After 1 hour at 0°, 0.90 ml of 37% aqueous formaldehyde (Formalin) was added dropwise over 5 minutes (0.90 ml=.36 g=12 mmol=3 eq.). The mixture was warmed to room temperature and stirred at room temperature for 2 hours.

The reaction was quenched at 0° by addition of 20 mL ethyl acetate and 5 mL 1N HCl. The organic layer was removed and the aqueous layer re-extracted with 5 mL ethyl acetate. The combined organic extracts were washed with 2×5 mL brine then filtered through a plug of anhydrous sodium sulfate onto anhydrous magnesium sulfate. The solution was filtered and all volatiles removed under vacuum to afford a pale yellow oil which was purified by medium pressure liquid chromatography on silica, eluting with 9/1 ethyl acetate/acetonitrile. Purification in this manner afforded 1.181 g 3.33 mmol; 81%) of the title compound as a viscous oil.

| NMR (300 MHz, CDCl₃): δ | |
|---|---|
| 7.3-7.4(m, 5H) | 4.2(m, 1H) |
| 6.4(d, 1H) | 3.75(m, 6H) |
| 5.8(d, 1H) | 3.0(q, 2H) |
| 5.2(s, 2H) | 1.4(q, 3H) |
| 5.1(br s, 1H) | |
| Mass Spec (EI): | |
| M⁺ 355 (.5%) | |
| Elemental Analysis: | |
| calc. for C₁₆H₂₂NO₆P | found |
| C: 54.08 | 53.01 |
| H: 6.24 | 6.19 |
| N: 3.94 | 3.73 |

TLC: (ethylacetate/n-butanol/acetic acid/water; 1:1:): $R_f$=0.85.

EXAMPLE 28

1-Aminoethyl-(2-carboxy-3-chloro-n-propyl) Phosphinic Acid

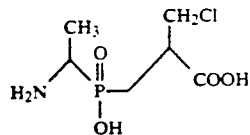

Methyl(1-Benzyloxycarbonylaminoethyl)-(2-carbomethoxy-2-propenyl)phosphinate from Example 27 (101 mg, 0.296 mmol) was suspended in 4 ml concentrated hydrochloric acid and heated at 50° for two weeks.

Reaction mixture diluted to 15 mL with distilled water and washed 3×5 mL with ethyl acetate. The aqueous layer was evaporated to dryness, the residue dissolved in 5 mL distilled water and freeze-dried to afford a pale yellow solid. The solid was dissolved in 1 mL absolute methanol and treated with excess propylene oxide. The precipitate was filtered off and dried under vacuum to afford 52 mg (0.23 mmol; 75%) of the title compound as a white powder.

| NMR (200 MHz, D$_2$O) δ | |
|---|---|
| 3.9(m, 2H) | 2.0(m, 1H) |
| 3.3(m, 2H) | 1.5(q, 3H) |
| 2.2(m, 1H) | |
| Mass Spec (NI-FAB) | |
| M − H 228 (100%) | |

EXAMPLE 29

1-Aminoethyl-(2-carboxy-5-phenyloct-2-enyl) phosphinic acid (E and Z isomers)

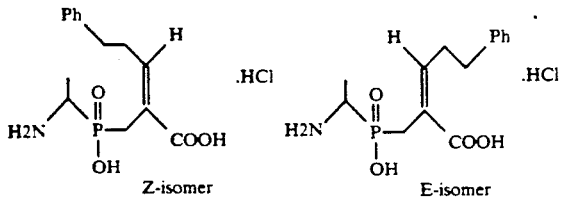

A. Methyl-1-benzyloxycarbonylaminoethyl-(2-carbomethoxy-5-phenyloct-2-enyl)phosphinate (E & Z isomers)

The title compounds were obtained from -benzyloxycarbonylaminoethylphosphonous acid methyl ester (1.054 gm, 4.1 mmol), 2-trimethylphosphonoacrylate (1.2 gm, 6.18 mmol), and phenylpropionaldehyde (1.63 gm, 12.2 mmol) by a method described in Example 27. Chromatographic separation (silica, 1, ethylacetate:acetonitrile) afforded the Z isomer of the title compound (0.929 gm) and the E isomer of the title compound (0.654 gm) as oils.

TLC (silica, 9:1:0.5, ethylacetate:acetonitrile: methanol) R$_f$=0.67 (both isomers).

| NMR (300 MHz, CDCl$_3$): | |
|---|---|
| Z isomer | E isomer |
| 7.2–7.4(m, 10H) | 7.2–7.4(m, 10H) |
| 7.0(m, 1H) | 6.2(m, 1H) |
| 5.5(d, .5H) | 5.4(d, .5H) |
| 5.1(m, 2.5H) | 5.1(m, 2.5H) |
| 4.1(m, 1H) | 4.1(m, 1H) |
| 3.7(m, 6H) | 3.7(m, 6H) |
| 2.6–3.0(m, 6H) | 2.7–3.0(m, 6H) |
| 1.3(m, 3H) | 1.3(m, 3H) |
| Mass Spec (EI): | |
| E isomer: 459(M+, 1%) | |
| Z isomer: 459(M+, 1%) | |

B. 1-Aminoethyl-(2-carboxy-5-phenyloct-2-enyl)-phosphinic acid (E & Z isomers)

Treatment of each of the E and Z isomers of methyl-1-benzyloxycarbonylaminoethyl(2-carbomethoxy-5-phenyloct-2-enyl)phosphinate with concentrated hydrochloric acid as described in Example 33 afforded the hydrochloride salts (66% yield for E isomer, 79% for Z isomer) of the title compounds as white powders.

TLC (silica, 1:1:1:1. ethylacetate:n-butanol:acetic acid:water) R$_f$ Z-isomer=0.59, E-isomer=0.57.

| NMR (200 MHz D$_2$O): | |
|---|---|
| Z isomer | E isomer |
| 7.2–7.4(m, 5H) | 7.2–7.4(m, 5H) |
| 6.8(m, 1H) | 6.0(m, 1H) |
| 3.3(m, 7H) | 3.1–3.3(m, 7H) |
| 1.3(q, 3H) | 1.3(q, 3H) |
| Mass Spec (NI FAB): | |
| E isomer: 296 (M − H, 100%) | |
| Z isomer: 296 (M − H, 100%) | |

EXAMPLE 30

1-Aminoethyl-(2-carboxy-oct-2-enyl)phosphinic acid (E/Z mixture)

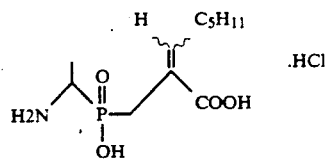

A. Methyl 1-t-butoxycarbonylaminoethyl-(2-carbomethoxy-oct-2-enyl)phosphinate (E/Z mixture)

The title compound was prepared form -t-butoxycarbonylaminoethylphosphonous acid methyl ester (0.616 gm, 2.76 mmol), (example 36) -trimethylphosphonoacrylate (1.08 gm, 5.54 mmol), and hexanal (0.55 gm, 5.5 mmol) by the method described in Example 27. the product was purified by chromatography (silica, 5% methanol in ethylacetate) to give the title compound (0.805 gm) as a mixture of E/Z isomers.

TLC (silica, 9:1:0.5, ethylacetate:acetonitrile: methanol) R$_f$=0.40.

| NMR (300 MHz, CDCl$_3$): | |
|---|---|
| 7.0(m, 5H, Z isomer) | 2.5(m, 1H) |
| 6.2(m, 5H, E isomer) | 2.3(m, 1H) |
| 5.0(m, 1H) | 1.9(m, 1H) |
| 4.1(m, 1H) | 1.5(s, 9H) |
| 3.7(m, 6H) | 1.3(m, 8H) |

| -continued | |
|---|---|
| 3.0(m, 2H) | 0.9(t, 3H) |
| Mass Spec (FAB): | |
| 392 (M − H, 38%) | |
| Elemental Analysis: | |
| calc. for C$_{18}$H$_{34}$NO$_6$P.½H$_2$O | found |
| C: 53.99 | 53.23 |
| H: 8.80 | 8.30 |
| N: 3.50 | 3.51 |

B. 1-Aminoethyl-(2-carboxy-1-oct-2-enyl)phosphinic acid (E/Z isomer mixture)

The title compound was prepared from Methyl-1-t-butoxycarbonylaminoethyl-(2-carbomethoxy-1-oct-2-enyl)phosphinate (0.176 gm, 0.45 mmol) by stirring in concentrated HCl according to Example 33. The title compound as its hydrochloride salt (0.105 gm) was obtained as a hygroscopic white powder.

TLC (silica, 1:1:1:1, ethylacetate:n-butanol:acetic:water) R$_f$=0.57.

| NMR (300 MHz, CD$_3$OD): | |
|---|---|
| 7.0(m, 5H, Z isomer) | 2.4(m, 1H) |
| 6.2(m, 5H, E isomer) | 2.2(m, 2H) |
| 3.3(m, 1H) | 1.2−1.5(m, 8H) |
| 2.8(m, 2H) | 0.8(br s, 3H) |
| Mass Spec (NI FAB): | |
| 262 (M − H, 100%) | |

EXAMPLE 31

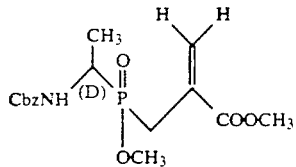

Methyl(1-D-Benzyloxycarbonylamino)ethyl)-(2-carbomethoxy-2-propenyl)phosphinate

A solution of 1.0405 g (4.05 mmol) -(D)-benzyloxycarbinylaminoethylphosphonous acid methyl ester in 2.5 mL distilled methanol at 0° was treated dropwise over 10 minutes with 2.2 mL of 2.0N methanolic sodium methoxide (4.4 mmol; 1.1 eq.). When the addition of base was complete, the mixture was stirred an additional 5 minutes at 0° before a solution of 0.94 ml (1.18 g, 6.1 mmol, 1.5 eq.) trimethyl-2-phosphonoacrylate (Fluka) in 1 ml distilled methanol was added dropwise over 5 minutes. After 1 hour at 0°, 0.93 ml of 37% aqueous formaldehyde (Formalin) was added dropwise over 5 minutes (0.93 ml=0.37 g =12 mmol =3 eq.). The mixture was warmed to room temperature and stirred at room temperature for 3 hours.

The reaction was quenched at 0° by addition of 20 mL ethylacetate and 5 mL 1% HCl. The organic layer was removed and the aqueous layer re-extracted with 5 mL ethylacetate. The combined organic extracts were washed on 2×5 mL brine then filtered through a plug of anhydrous sodium sulfate onto anhydrous magnesium sulfate. The solution was filtered and all volatiles removed under vacuum to afford a pale yellow oil which was purified by medium pressure liquid chromatography on silica, eluting with 5% methanol/ethylacetate. Purification in this manner afforded 1.091 g (3.07 mmol; 75%) of pure title compound as a viscous oil.

| NMR (300 MHz, CD$_3$OD): | |
|---|---|
| 7.3−7.4(m, 5H,) | 4.2(m, 1H) |
| 6.4(d, 1H) | 3.75(m, 6H) |
| 5.8(d, 1H) | 3.0(dd, 2H) |
| 5.2(s, 2H) | 1.4(dd, 3H) |
| 5.1(brs, 1H) | |
| Mass Spec (EI): | |
| 355(.5%), M$^+$ | |
| Elemental Analysis: | |
| calc. for C$_{16}$H$_{22}$NO$_6$P.½H$_2$O | found |
| C: 52.75 | 53.01 |
| H: 6.36 | 6.19 |
| N: 3.85 | 3.73 |
| R$_f$(ethylacetate/n-butanol/ acetic acid/water; 1:1:1:1): | .85 |

EXAMPLE 32

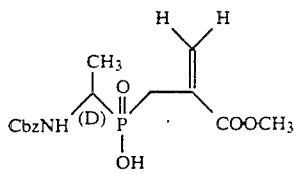

(1-D-Benzyloxycarbonylamino)ethyl)-(2-carbomethoxy-2-propenyl)phosphinic acid

Under nitrogen, a solution of Methyl(1-D-Benzyloxycarbonylaminoethyl)-(2-carbomethoxy-2-Propenyl)-phosphinate (2.26 g, 6.34 mmol) in 10 mL dry THF at room temperature was treated with 0.94 g (7.0 mmol, 1.1 eq.) anhydrous lithium iodide. The mixture was stirred at room temperature for 72 hours at which time tlc (ethylacetate/n-butanol/acetic acid/water; 1:1:1:1) indicated complete absence of starting material with appearance of the product with Rf of 0.70.

All volatiles were removed under vacuum and the residue redissolved in 30 mL 5% aqueous sodium bicarbonate and washed with ethylacetate (5×10 mL). The aqueous layer was cooled to 0° and made acidic (pH 1) by the slow addition of 6N HCl. The acidified mixture was extracted with ethylacetate (6 x 10 mL); the combined organic extracts washed once with brine and filtered through a plug of anhydrous sodium sulfate onto anhydrous magnesium sulfate. Filtration and removal of solvent in vacuo afforded the title compound (1.779 g, 5.22 mmol, 82%) as a pale yellow solid.

| NMR (300 MHz, CD$_3$OD): δ | |
|---|---|
| 7.3−7.4(m, 6H,) | 4.0(m, 1H) |
| 6.3(d, 1H, ) | 3.7(m, 3H) |
| 5.8(d, 1H) | 3.0(d, 2H) |
| 5.1(br s, 2H) | 1.3(dd, 3H) |
| Mass Spec (FAB): | |
| 342 (100%), M + H | |
| Elemental Analysis: | |
| calc. for C$_{15}$H$_{20}$NO$_6$P.½H$_2$O | found |
| C: 51.43 | 51.09 |
| H: 6.03 | 5.67 |
| N: 4.00 | 4.02 |
| R$_f$(ethylacetate/n-butanol/ acetic acid/water; 1:1:1:1): | 0.70 |

EXAMPLE 33

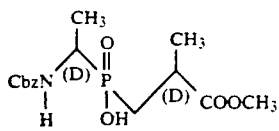

(1-D-Benzyloxycarbonylaminoethyl)-(2-carbomethoxy-2-D-methyl-1-ethyl)phosphinic Acid A solution of 0.172 g 0.504 mmol) of 1-D-Benzyloxycarbonylaminoethyl)-(2-carbomethoxy-2-propenyl)-phosphinic acid in 3 mL of dry methanol and 0.5 mL of benzene was hydrogenated at 40 psi in the presence of 25 mg of 1,5 cyclooctadiene-rhodium (I) chloride dimer and 70 mg of (−)2,3–0-isopropylidene-2,3-dihydroxy-1,4-(diphenylphosphino)butane ( (−) DIOP) . Hydrogen uptake was complete after 3 hours. The mixture was diluted with 10 mL of ether, cooled to 0° C. and filtered to remove product. The crude product was recrystallized 3 times from aqueous acetic acid to give the title compound.

| NMR (300 MHz, CD$_3$OD): δ | |
|---|---|
| 7.3–7.5(m, 6H) | 2.2(m, 1H) |
| 5.1(dd, 1H) | 1.8(m, 1H) |
| 4.0(m, 1H) | 1.3(dd, 3H) |
| 3.7(s, 3H) | 1.2(d, 3H) |
| 2.9(m, 1H) | |
| Mass Spec (NI FAB): | |
| 342(40%), M − H | |
| Elemental Analysis: | |
| calc. for C$_{15}$H$_{20}$NO$_6$P | found |
| C: 52.48 | 52.49 |
| H: 6.46 | 6.16 |
| N: 4.08 | 4.25 |
| R$_f$(ethylacetate/n-butanol/ acetic acid/water: 1:1:1:1): | 0.70 |

EXAMPLE 34

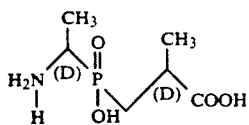

(1-D-Aminoethyl)-(2-carboxy-2-D-methyl-1-ethyl)-phosphinic acid (1-D-Benzyloxycarbonylaminoethyl)-(2-carbomethoxy-2-D-methyl-1-ethyl)phosphinic acid was converted to the title compound in 60% yield by procedures described in Example 2.

| NMR (300 MHz, D$_2$O): δ | |
|---|---|
| 3.25(m, 1H,) | 1.68(m, 1H) |
| 2.81(d, 1H,) | 1.38(dd, 3H) |
| 2.10(d, 1H) | 1.27(d, 3H) |
| Mass Spec (NI FAB): | |
| 194(55%), M − H | |
| R$_f$(ethylacetate/n-butanol/ acetic acid/water: 1:1:1:1): | 0.35 |

EXAMPLE 35

1-Aminoethyl-(2-carboxy-(4-phenyl-2-Z-butenyl))phosphinic acid

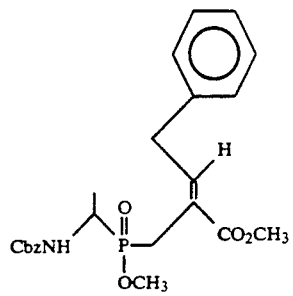

A.
Methyl(1-Benzyloxycarbonylaminoethyl)-(2-carbomethoxy-(4-phenyl-2-Z-butenyl))phosphinate The title compound was prepared from 1-benzyloxycarbonylaminoethylphosphonous acid methyl ester (1.154 gm, 4.49 mmol), 2-trimethylphosphonoacrylate (1.31 g, 6.7 mmol), and phenylacetaldehyde (1.08 gm, 8.9 mmol) by the procedure described in Example 29. The crude product was purified by chromatography (silica, 9:1, ethylacetate:acetonitrile) to give 0.41 gm of the title compound.

TLC (silica, 9:1:0.5, ethylacetate:acetonitrile: methanol). R$_f$=0.70.

| NMR (300 MHz, CD$_3$Cl$_3$): δ | |
|---|---|
| 7.0–7.4(m, 11H,) | 3.7(m, 6H) |
| 5.5(d, .5H) | 3.6(m, 2H) |
| 5.1(m, 2.5H) | 3.1(m, 2H) |
| 4.1(m, 1H) | 1.4(q, 3H) |
| Mass Spec (FAB): | |
| 446 (M + H, 100%) | |
| Elemental Analysis: | |
| calc. for C$_{23}$H$_{28}$NO$_6$P.½H$_2$O | found |
| C: 60.79 | 60.03 |
| H: 6.43 | 6.11 |
| N: 3.08 | 3.14 |

B.
1l-Aminoethyl-(2-carboxy-(4-phenyl-2-Z-butenyl))-phosphinic acid

1-Benzyloxycarbonylaminoethyl-(2-carbomethoxy-(4-phenyl-2-Z-butenyl)phosphinic acid methyl ester (0.1 gm, 0.23 mmol) was stirred for 1 week in concentrated HCl (5 mL). After concentration in vacuo, the hydrochloride salt of the title compound (0.051 gm) was obtained as a white powder. TLC (silica, 1:1:1:1, ethylacetate:n-butanol:acetic acid:water) R$_f$=0.43.

| NMR (200 MHz, D$_2$O): δ | |
|---|---|
| 7.0–7.8(m, 6H,) | 3.0(m, 2H) |
| 3.7(m, 2H) | 1.5(q, 3H) |
| 3.4(m, 1H) | |
| Mass Spec (NI FAB): | |
| 282 (M − H, 55%) | |

EXAMPLE 36

1-t-Butoxycarbonylaminoethylphosphonous acid methylester

The title compound was prepared in 63% yield according to the procedures described in Example 1 with the only variant being that di-t-butyldicarbonate was used to protect the amino group in place of benzylchloroformate. The title compound was purified by chromatography (silica, 9:,ethylacetate:acetonitrile).

TLC (silica, 10:1,ethylacetate:ethanol) $R_f = 0.70$.

NMR (300MHz, CDCl$_3$) 1.3 (m, 3H); 1.4 (s, 9H); 3.8 (d, 3H); 4.0 (m, 1H); 4.8 (br d, 1H); 6.1 (s, 0.5H) 7.9 (s, 0.5 H).

What is claimed is:

1. A compound of the formula:

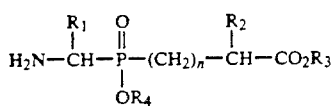

wherein:

$R_1$ is
  H, CH$_3$;

$R_2$ is
  (a) hydrogen,
  (b) C$_1$-C$_{12}$ linear or branched alkyl;
  (c) C$_2$-C$_{12}$ linear or branched monoalkenyl; or
  (d) C$_7$-C$_{20}$ aralkyl, wherein the alkyl chain is linear or branched C$_1$-C$_8$;
  wherein said above values for $R_2$ can be substituted by a substituent selected from the group consisting of: halo, hydroxy, carboxy, C$_1$-C$_4$ alkoxycarbonyl, C$_7$-C$_{16}$ arylalkoxycarbonyl, C$_3$-C$_7$ cycloalkyl, C$_1$-C$_4$ alkoxy, C$_6$-C$_{12}$ aryloxy, amino, mono- or di-C$_1$-C$_8$ alkylamino, thio, C$_1$-C$_4$ alkylthio, C$_6$-C$_{12}$ arylthio, C$_7$-C$_{16}$ aralkylthio, or the radical —S—(CH$_2$)$_n$—CH(NH$_2$)COOH, where n=1-2; with the proviso that $R_2$ is at least C$_2$ alkyl if substituted by one of the above-defined thio groups, and wherein the aryl can be further substituted by C$_1$-C$_4$ linear or branched alkyl, trihalomethyl, nitro, cyano or sulfonamido, halo;

$R_3$ and $R_4$ are hydrogen, C$_1$-C$_4$ alkyl, aryl selected from the group consisting of phenyl, naphthyl and biphenyl or aralkyl having one to eight carbon atoms in the alkyl portion and an aryl portion selected from the group consisting of phenyl, naphthyl or biphenyl;

and including steroisomers and racemates thereof.

2. The compound of claim 1 wherein:
$R_1$ is
methyl;
$R_2$
  C$_1$-C$_{10}$ linear or branched alkyl;
  C$_7$-C$_{14}$ aralkyl;
  wherein both groups can be substituted with halo, amino, mono- or di-C$_1$-C$_4$ linear or branched alkylamino, carboxyl, C$_1$-C$_4$ alkoxycarbonyl, hydroxy, C$_1$-C$_4$ alkoxy, C$_5$-C$_6$ cycloalkyl, C$_6$-C$_{10}$ aryloxy, thio, C$_1$-C$_4$ linear or branched alkylthio, C$_6$-C$_{10}$ arylthio, C$_7$-C$_{14}$ aralkylthio, —S—(CH$_2$)$_n$—CH(NH$_2$)CO$_2$H, where n=1-2, with the proviso that $R_2$ or $R_5$ is at least C$_2$ alkyl if substituted by one of the above-defined thio groups and wherein the aryl groups can further be substituted by linear or branched C$_1$-C$_4$ alkyl; $R_3$ and $R_4$ are hydrogen, benzyl.

3. The compound of claim 1 in which the stereochemical configurations of the carbon attached to $R_1$, and the carbon attached to $R_2$, are respectively, D(S), DL(SR) or D(R),DL(RS).

4. The compound of claim 3 in which the stereochemical configurations of the carbons attached to $R_1$ and $R_2$ are D(S), D(R) respectively.

5. The compound of claim 1 in which the stereochemical configurations of the carbons attached to $R_1$ and $R_2$ are L(R) and D(R), L(S), DL(RS), respectively.

6. The compound of claim 2 which is 1-aminoethyl-(2-carboxypropyl) phosphinic acid.

7. The compound of claim 2 which is 1-(aminoethyl)-(2-carbomethoxy-propyl)-phosphinic acid.

8. The compound of claim 2 which is 1-(aminoethyl)-(2-carboxy-n-butyl) phosphinic acid.

9. The compound of claim 2 which is 1-(aminoethyl)-(2-carboxy-5-phenyl-n-pentyl) phosphinic acid.

10. The compound of claim 2 which is 1-(aminoethyl)-(2-carboxy-n-nonyl) phosphinic acid.

11. The compound of claim 2 which is 1-(aminoethyl)-(2-carboxy-3-chloro-n-propyl) phosphinic acid.

12. The compound of claim 2 which is 1-(aminoethyl)-(2-carboxy-3-bromo-n-propyl) phosphinic acid.

13. The compound of claim 2 which is 1-(aminoethyl)-(2-carboxy-n-hexyl) phosphinic acid.

* * * * *